(12) United States Patent
Went et al.

(10) Patent No.: US 8,987,333 B2
(45) Date of Patent: *Mar. 24, 2015

(54) COMPOSITION AND METHOD FOR TREATING NEUROLOGICAL DISEASE

(71) Applicant: Adamas Pharmaceuticals, Inc., Emeryville, CA (US)

(72) Inventors: Gregory T. Went, Mill Valley, CA (US); Timothy J. Fultz, Jasper, GA (US); Seth Porter, San Carlos, CA (US); Laurence R. Meyerson, Las Vegas, NV (US); Timothy S. Burkoth, Lake Bluff, IL (US)

(73) Assignee: Adamas Pharmaceuticals, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/451,262

(22) Filed: Aug. 4, 2014

(65) Prior Publication Data

US 2014/0356425 A1    Dec. 4, 2014

Related U.S. Application Data

(63) Continuation of application No. 14/328,440, filed on Jul. 10, 2014, now Pat. No. 8,895,614, which is a continuation of application No. 13/958,153, filed on Aug. 2, 2013, now Pat. No. 8,796,337, which is a continuation of application No. 13/756,275, filed on Jan. 31, 2013, now abandoned, which is a continuation of application No. 11/286,448, filed on Nov. 23, 2005, now Pat. No. 8,389,578.

(60) Provisional application No. 60/631,095, filed on Nov. 24, 2004.

(51) Int. Cl.

| | |
|---|---|
| A61K 31/13 | (2006.01) |
| A61K 31/195 | (2006.01) |
| A61K 31/198 | (2006.01) |
| A61K 31/197 | (2006.01) |
| A61K 9/16 | (2006.01) |
| A61K 9/20 | (2006.01) |
| A61K 9/28 | (2006.01) |
| A61K 9/50 | (2006.01) |
| A61K 45/06 | (2006.01) |
| A61K 9/00 | (2006.01) |
| A61K 9/48 | (2006.01) |

(52) U.S. Cl.
CPC ............. *A61K 31/13* (2013.01); *A61K 31/197* (2013.01); *A61K 9/1617* (2013.01); *A61K 9/1652* (2013.01); *A61K 9/2009* (2013.01); *A61K 9/2054* (2013.01); *A61K 9/2846* (2013.01); *A61K 9/5047* (2013.01); *A61K 9/5078* (2013.01); *A61K 31/198* (2013.01); *A61K 45/06* (2013.01); *A61K 9/0004* (2013.01); *A61K 9/4808* (2013.01); *A61K 9/16* (2013.01)

USPC .......................................... 514/565; 514/656

(58) Field of Classification Search
CPC ....................................................... A61K 31/13
USPC .................................................. 514/565, 656
See application file for complete search history.

(56) References Cited

U.S. PATENT DOCUMENTS

| | | |
|---|---|---|
| 4,148,896 A | 4/1979 | Smith et al. |
| 4,606,909 A | 8/1986 | Bechgaard et al. |
| 4,769,027 A | 9/1988 | Baker et al. |
| 4,812,481 A | 3/1989 | Reischig et al. |
| 4,828,836 A | 5/1989 | Elger et al. |
| 4,839,177 A | 6/1989 | Colombo et al. |
| 4,897,268 A | 1/1990 | Tice et al. |
| 5,057,321 A | 10/1991 | Edgren et al. |
| 5,190,763 A | 3/1993 | Edgren et al. |
| 5,192,550 A | 3/1993 | Edgren et al. |
| 5,221,536 A | 6/1993 | Edgren et al. |
| 5,330,766 A | 7/1994 | Morella et al. |
| 5,334,618 A | 8/1994 | Lipton |
| 5,358,721 A | 10/1994 | Guittard et al. |
| 5,366,738 A | 11/1994 | Rork et al. |
| 5,382,601 A | 1/1995 | Numberg et al. |
| 5,395,626 A | 3/1995 | Kotwal et al. |
| 5,422,123 A | 6/1995 | Conte et al. |
| 5,576,022 A | 11/1996 | Yang et al. |
| 5,601,845 A | 2/1997 | Buxton et al. |
| 5,614,560 A | 3/1997 | Lipton et al. |
| 5,849,800 A | 12/1998 | Smith |
| 5,891,885 A | 4/1999 | Caruso |
| 5,912,013 A | 6/1999 | Rudnic et al. |

(Continued)

FOREIGN PATENT DOCUMENTS

| | | |
|---|---|---|
| EP | 1600156 A2 | 11/2005 |
| EP | 1845968 A2 | 11/2005 |

(Continued)

OTHER PUBLICATIONS

U.S. Appl. No. 13/863,140, filed Apr. 15, 2013, Went et al.

(Continued)

*Primary Examiner* — Paul Zarek
(74) *Attorney, Agent, or Firm* — Wilson Sonsini Goodrich & Rosati

(57) ABSTRACT

Disclosed are compositions comprising amantadine, or a pharmaceutically acceptable salt thereof, and one or more excipients, wherein at least one of the excipients modifies release of amantadine. Methods of administering the same are also provided.

11 Claims, 7 Drawing Sheets

(56) References Cited

U.S. PATENT DOCUMENTS

| | | |
|---|---|---|
| 5,919,826 A | 7/1999 | Caruso |
| 6,187,338 B1 | 2/2001 | Caruso et al. |
| 6,194,000 B1 | 2/2001 | Smith et al. |
| 6,217,905 B1 | 4/2001 | Edgren et al. |
| 6,284,276 B1 | 9/2001 | Rudnic et al. |
| 6,384,083 B1 | 5/2002 | Ludwig et al. |
| 6,479,553 B1 | 11/2002 | McCarthy |
| 6,491,949 B2 | 12/2002 | Faour et al. |
| 6,569,463 B2 | 5/2003 | Patel et al. |
| 6,764,697 B1 | 7/2004 | Jao et al. |
| 6,919,373 B1 | 7/2005 | Lam et al. |
| 6,923,800 B2 | 8/2005 | Chen et al. |
| 7,619,007 B2 | 11/2009 | Went et al. |
| 7,858,660 B2 | 12/2010 | Nguyen et al. |
| 7,981,930 B2 | 7/2011 | Nguyen et al. |
| 8,058,291 B2 | 11/2011 | Went et al. |
| 8,168,209 B2 | 5/2012 | Went et al. |
| 8,173,708 B2 | 5/2012 | Went et al. |
| 8,252,331 B2 | 8/2012 | Meyer et al. |
| 8,283,379 B2 | 10/2012 | Went et al. |
| 8,293,794 B2 | 10/2012 | Went et al. |
| 8,329,752 B2 | 12/2012 | Went et al. |
| 8,338,485 B2 | 12/2012 | Went et al. |
| 8,338,486 B2 | 12/2012 | Went et al. |
| 8,362,085 B2 | 1/2013 | Went et al. |
| 8,389,578 B2 | 3/2013 | Went et al. |
| 8,426,472 B2 | 4/2013 | Went et al. |
| 8,574,626 B2 | 11/2013 | Vergez et al. |
| 8,580,858 B2 | 11/2013 | Went et al. |
| 8,598,233 B2 | 12/2013 | Went et al. |
| 8,741,343 B2 | 6/2014 | Went et al. |
| 8,796,337 B2 | 8/2014 | Went et al. |
| 8,889,740 B1 | 11/2014 | Went et al. |
| 8,895,614 B2 | 11/2014 | Went et al. |
| 8,895,615 B1 | 11/2014 | Went et al. |
| 8,895,616 B1 | 11/2014 | Went et al. |
| 8,895,617 B1 | 11/2014 | Went et al. |
| 8,895,618 B1 | 11/2014 | Went et al. |
| 2001/0031278 A1 | 10/2001 | Oshlack et al. |
| 2002/0071863 A1 | 6/2002 | Dong et al. |
| 2003/0045577 A1 | 3/2003 | Madhat |
| 2003/0170302 A1 | 9/2003 | Seth et al. |
| 2003/0203055 A1 | 10/2003 | Rao et al. |
| 2004/0087658 A1 | 5/2004 | Moebius |
| 2004/0097484 A1 | 5/2004 | Cantillion et al. |
| 2004/0102525 A1 | 5/2004 | Kozachuk |
| 2004/0106681 A1 | 6/2004 | Rao et al. |
| 2004/0122090 A1 | 6/2004 | Lipton |
| 2004/0224020 A1 | 11/2004 | Schoenhard |
| 2005/0031651 A1 | 2/2005 | Gervais et al. |
| 2005/0065219 A1 | 3/2005 | Lipton et al. |
| 2005/0119249 A1 | 6/2005 | Buntinx |
| 2005/0124701 A1 | 6/2005 | Went et al. |
| 2005/0153953 A1 | 7/2005 | Trippodi-Murphy et al. |
| 2005/0191349 A1 | 9/2005 | Boehm et al. |
| 2005/0208132 A1 | 9/2005 | Sathyan et al. |
| 2005/0209218 A1 | 9/2005 | Meyerson et al. |
| 2005/0232990 A1 | 10/2005 | Boehm et al. |
| 2005/0245460 A1 | 11/2005 | Meyerson et al. |
| 2005/0245617 A1 | 11/2005 | Meyerson et al. |
| 2006/0052370 A1 | 3/2006 | Meyerson et al. |
| 2006/0063810 A1 | 3/2006 | Vergez et al. |
| 2006/0142398 A1 | 6/2006 | Went et al. |
| 2006/0159763 A1 | 7/2006 | Meyer et al. |
| 2006/0189694 A1 | 8/2006 | Went et al. |
| 2006/0240043 A1 | 10/2006 | Meyerson et al. |
| 2006/0252788 A1 | 11/2006 | Went et al. |
| 2010/0260838 A1 | 10/2010 | Went et al. |
| 2010/0266684 A1 | 10/2010 | Went et al. |
| 2010/0311697 A1 | 12/2010 | Went et al. |
| 2011/0059169 A1 | 3/2011 | Went et al. |
| 2011/0064804 A1 | 3/2011 | Went et al. |
| 2011/0189273 A1 | 8/2011 | Went et al. |
| 2011/0230432 A1 | 9/2011 | Nguyen et al. |
| 2012/0045508 A9 | 2/2012 | Went et al. |
| 2012/0046365 A1 | 2/2012 | Went et al. |
| 2012/0288560 A1 | 11/2012 | Went et al. |
| 2013/0115249 A1 | 5/2013 | Vergez et al. |
| 2013/0165517 A1 | 6/2013 | Went et al. |
| 2013/0317115 A1 | 11/2013 | Went et al. |
| 2014/0134243 A1 | 5/2014 | Went et al. |
| 2014/0179797 A1 | 6/2014 | Went et al. |
| 2014/0242163 A1 | 8/2014 | Went et al. |
| 2014/0323582 A1 | 10/2014 | Went et al. |
| 2014/0343152 A1 | 11/2014 | Went et al. |
| 2014/0343153 A1 | 11/2014 | Went et al. |
| 2014/0343154 A1 | 11/2014 | Went et al. |
| 2014/0343163 A1 | 11/2014 | Went et al. |
| 2014/0343164 A1 | 11/2014 | Went et al. |

FOREIGN PATENT DOCUMENTS

| | | |
|---|---|---|
| EP | 1827385 A2 | 9/2007 |
| EP | 2343057 A1 | 7/2011 |
| EP | 1827385 B1 | 3/2013 |
| EP | 2623099 A1 | 8/2013 |
| JP | 2002-506047 | 2/2002 |
| WO | WO 94/05275 A1 | 3/1994 |
| WO | WO 97/14415 A1 | 4/1997 |
| WO | WO 98/18457 A1 | 3/1998 |
| WO | WO 99/45963 A1 | 9/1999 |
| WO | WO 00/00197 | 1/2000 |
| WO | WO 00/18378 A1 | 4/2000 |
| WO | WO 2004/087116 A3 | 12/2000 |
| WO | WO 01/19901 A2 | 3/2001 |
| WO | WO 01/32148 A1 | 5/2001 |
| WO | WO 01/19901 A3 | 9/2001 |
| WO | WO 2004/087116 A2 | 10/2004 |
| WO | WO 2005/072705 A1 | 8/2005 |
| WO | WO 2005/079773 A2 | 9/2005 |
| WO | WO 2005/079773 A3 | 10/2005 |
| WO | WO 2006/058059 A2 | 6/2006 |
| WO | WO 2006/058236 A2 | 6/2006 |
| WO | WO 2006/058059 A3 | 7/2006 |
| WO | WO 2006/089494 A1 | 8/2006 |

OTHER PUBLICATIONS

U.S. Appl. No. 14/052,507, filed Oct. 11, 2013, Went et al.

Anand et al., "Dissolution Testing: An FDA Perspective," AAPS Workshop, Physical Pharmacy and Biopharmaceutics, May 13, 2009, 1-32.

Antonelli, et al. Experimental studies and theoretical aspects on A2A/D2 receptor interactions in a model of Parkinson's disease. Relevance for L-dopa induced dyskinesias. J Neurol Sci 2006;248:16-22.

Bandini, et al. The visuo-cognitive and motor effect of amantadine in non-Caucasian patients with Parkinson's disease. A clinical and electrophysiological study. J Neural Transm. 2002;109(1):41-51.

Bara-Jimenez, et al. Effects of serotonin 5-HT1A agonist in advanced Parkinson's disease. Mov Disord 2005;20:932-936.

Bibbiani, et al. Serotonin 5-HT1A agonist improves motor complications in rodent and primate parkinsonian models. Neurology 2001;27:1829-1834.

Blanpied, et al. Trapping channel block of NMDA-activated responses by amantadine and memantine. J Neurophysiol. Jan. 1997;77(1):309-23.

Bonnett, A. Involvement of Non-Dopaminergic Pathways in Parkinson's Disease: Pathophysiology and Therapeutic Implications. CNS Drugs, vol. 13, No. 5, May 2000 , pp. 351-364(14).

Budziszewska, et al. Antidepressant drugs inhibit glucocorticoid receptor-mediated gene transcription—a possible mechanism. Br J Pharmacol. Jul. 2000;130(6):1385-93.

Cersosimo, et al. Amantadine for the treatment of levodopa dyskinesias in Parkinson's disease. Medicina (B Aires). 2000;60(3):321-5. (full English translation).

Colomiso, et al. Task Force Report on Scales to Assess Dyskinesia in Parkinson's Disease: Critique and Recommendations. Movement Disorders, 2010, p. 1-12.

Crosby, et al. Amantadine for dyskinesia in Parkinson's disease. Cochrane Database of Systematic Reviews 2003, Issue 2. Art. No. CD003467. DOI: 10.1002/14651858.CD003467.

(56) References Cited

OTHER PUBLICATIONS

Crosby, et al. Amantadine in Parkinson's disease. Cochrane Database of Systematic Reviews 2003, Issue 1. Art. No. CD003468. DOI: 10.1002/14651858.CD003468.
Da Silva-Junior, et al. Amantadine reduces the duration of levodopa-induced dyskinesia: A randomized, double-blind, placebo-controlled study. Parkinsonism Relat Disord. Nov. 2005;11(7):449-52.
Danysz, et al. Aminoadamantanes as NMDA receptor antagonists and antiparkinsonian agents—preclinical studies. Neurosci. Biobehav. Rev. 1997;21(4):455-468.
Del Dotto, et al. Intravenous amantadine improves levadopa-induced dyskinesias: an acute double-blind placebo-controlled study. Mov Disord. May 2001;16(3):515-20.
Engber, et al. NMDA receptor blockade reverses motor response alterations induced by levodopa. Neuroreport. Dec. 20, 1994;5(18):2586-8.
European search report dated Jun. 10, 2011 for EP 10179758.7.
Fachinfo-Service: Amantadin-CT 100 mg Filmtabletten. 2004, Rote Liste Service GmBh, Berlin (in German with English translation).
Fahn, et al. Long-term evaluation of amantadine and levodopa combination in parkinsonism by double-blind crossover analyses. Neurology. Aug. 1975;25(8):695-700.
Fehling, C. The effect of adding amantadine to optimum L-dopa dosage in Parkinson's syndrome. Acta Neurol Scand. 1973;49(2):245-51.
Fredriksson, et al. Co-administration of memantine and amantadine with sub/suprathreshold doses of L-Dopa restores motor behaviour of MPTP-treated mice. J Neural Transm. 2001;108(2):167-87.
Goetz, et al. Sarizotane as a treatment of dykinesias in parkinson's disease: a double-blind Placebo controlled trial. Mov Disord 2007;22:179-186.
Greenamyre, et al. Antiparkinsonian effects of remacemide hydrochloride, a glutamate antagonist, in rodent and primate models of Parkinson's disease. Ann Neurol. Jun. 1994;35(6):655-61.
Greenberg, et al. Treatment of Major Depression and Parkinson's Disease with Combined Phenelzine and Amantadine. Am. J. Psychiatry. 1985;142(2):273-274.
Guttman, et al. Current concepts in the diagnosis and management of Parkinson's disease. CMAJ. Feb. 4, 2003;168(3):293-301.
Hayden, "Differences in Side Effects of Amantadine Hydrochloride and Rimantadine Hydrochloride Relate to Differences in Pharmacokinetics," AAC, 23(3) 1983, pp. 458-464.
Hayden, et al. Comparative Toxicity of Amantadine Hydrochloride and Rimantadine Hydrochloride in Healthy Adults. Antimicrobial Agents and Chemotherapy, vol. 19, No. 2, Feb. 1981, p. 226-233.
Ing et al., "Toxic Effects of Amantadine in Patients with Renal Failure," CMA Journal, Mar. 1979, vol. 120, pp. 695-697.
International search report dated Feb. 7, 2011 for PCT/US2010/058789.
International search report dated Aug. 9, 2006 for PCT Application No. US2005/42780.
Jackson, et al. Chemoprophylaxis of viral respiratory diseases. Pan American Health Organization. 1967;595-603.
Jenner, P. Preventing and controlling dyskinesia in Parkinson's disease—a view of current knowledge and future opportunities. Mov Disord. 2008;23 Suppl 3:S585-98.
Klockgether, et al. NMDA antagonists potentiate antiparkinsonian actions of L-dopa in monoamine-depleted rats. Ann Neurol. Oct. 1990;28(4):539-46.
Konitsiotis, et al. AMPA receptors blockade improves levodopa-induced dyskinesia in MPTP monkeys. Neurology 2000;54:1589-1595.
Kornhuber, et al. Amantadine and Memantine are NMDA receptor antagonists with neuroprotective properties. J Neural Transm Suppl. 1994;43:91-104.
Lewitt, et al. Adenosine A2A receptor antagonist istradefylline (KW-6002) reduces "off" time in Parkinson's disease: a double-blind, randomized, multicenter clinical trial (6002-US-005). Ann Neurol 2008;63:295-302.

Luginger, et al. Beneficial effects of amantadine on L-dopa-induced dyskinesias in Parkinson's disease. Mov Disord. Sep. 2000;15(5):873-8.
Manson, et al. Idazoxan is ineffective for levodopa-induced dyskinesias in Parkinson's disease. Mov Disord 2000;15:336-337.
Marcea, et al. Effect of Memantine versus dh-Ergotoxin on Cerebroorganic Psycho-syndrome. Therapiewoche. 1988;38:3097-3100 (with English summary).
McLean, et al. Prophylactic and therapeutic efficacy of memantine against seizures produced by soman in the rat. Toxicol Appl Pharmacol. Jan. 1992;112(1):95-103.
Merims, et al. Riluzole for levodopa-induced dyskinesias in advanced Parkinson's disease. Lancet. May 22, 1999;353(9166):1764-5.
Metman, et al. A trial of dextromethorphan in parkinsonian patients with motor response complications. Mov Disord. May 1998;13(3):414-7.
Metman, et al. Amantadine as treatment for dyskinesias and motor fluctuations in Parkinson's disease. Neurology. May 1998;50(5):1323-6.
Metman, et al. Amantadine for levodopa-induced dyskinesias: a 1-year follow-up Study. Arch Neurol 1999;56:1383-1386.
Moryl, et al. Potential antidepressive properties of amantadine, memantine and bifemelane. Pharmacol. Toxicol. 1993;72(6):394-397.
Olanow, et al. Multicenter, openlabel, trial of sarizotan in Parkinson disease patients with levodopa-induced dyskinesias (the SPLENDID Study). Clin Neuropharmacol 2004;27:58-62.
Pahwa, et al. Practice Parameter: treatment of Parkinson disease with motor fluctuations and dyskinesia (an evidence-based review): report of the Quality Standards Subcommittee of the American Academy of Neurology. Neurology. Apr. 11, 2006;66(7):983-95.
Papa, et al. Levodopa-induced dyskinesias improved by a glutamate antagonist in Parkinsonian monkeys. Ann Neurol. May 1996;39(5):574-8.
Parkes, et al. Amantadine dosage in treatment of Parkinson's disease. The Lancet. 1970; 295:1130-1133.
Parkes, et al. Treatment of Parkinson's disease with amantadine and levodopa. A one-year study. Lancet. May 29, 1971;1(7709):1083-7.
Rajput, et al. New use for an old drug: amantadine benefits levodopa induced dyskiensias. Mov Disord 1998;13:851-854.
Rascol, et al. Idazoxan, an alpha-2 antagonist, and L-DOPA-induced dyskinesias in patients with Parkinson's disease. Mov Disord 2001;16:708-713.
Rausch, et al. Effects of L-deprenyl and amantadine in an MPTP-model of parkinsonism. J. Neural Transm. 1990;32:269-275.
Ruzicka, et al. Amantadine infusion treatment of motor fluctuations and dyskinesias in Parkinson's disease. J Neural Trans 2000;102:1297-1306.
Savery, F. Amantadine and a fixed combination of levodopa and carbidopa in the treatment of Parkinson's disease. Dis Nerv Syst. Aug. 1977;38(8):605-8.
Schwab, et al. Amantadine in Parkinson's Disease Review of More Than Two Years' Experience. JAMA, vol. 222, No. 7, Nov. 13, 1972, p. 792-795.
Schwab, et al. Amantadine in the treatment of Parkinson's disease. JAMA. May 19, 1969;208(7):1168-70.
Shannon, et al. Amantadine and motor fluctuations in chronic Parkinson's disease. Clin Neuropharmacol. Dec. 1987;10(6):522-6.
Shefrin, SL. Therapeutic advances in idiopathic Parkinsonism. Expert Opin Investig Drugs. Oct. 1999;8(10):1565-1588.
Siemers, E. Recent progress in the treatment of Parkinson's disease. Comprehensive Therapy. 1992; 18(9):20-24.
Silver, et al. Livedo reticularis in Parkinson's disease patients treated with amantadine hydrochloride. Neurology. Jul. 1972;22(7):665-9.
Snow, et al. The effect of amantadine on levodopa-induced dyskinesias in Parkinson's disease: a double-blind, placebo-controlled study. Clin Neuropharmacol. Mar.-Apr. 2000;23(2):82-5.
Spieker, et al. The NMDA antagonist budipine can alleviate levodopa-induced motor fluctuations. Mov Disord. May 1999;14(3):517-9.

(56) References Cited

OTHER PUBLICATIONS

Standaert, et al. Chapter 22: Treatment of central nervous system degenerative disorders. Goodman and Gilman's the Pharmacological Basis of Therapeutics 10$^{th}$ Ed., Hardman Limbird and Gilman Eds., McGraw-Hill, New York, 2001.
Stedman's Medical Dictionary. 27th ed. Lippincott, Eilliams and Wilkins. Baltimore 2000.
Thanvi, et al. Long term motor complications of levodopa: clinical features, mechanisms, and management strategies. Postgrad Med J. Aug. 2004;80(946):452-8.
Thomas, et al. Duration of amantadine benefit on dyskinesia of severe Parkinson's disease. J Neurol Neurosurg Psychiatry 2004;75:141-143.
Vale, et al. Amantadine in depression. Lancet. 1971; 11:437.
Walker, et al. A qualitative and quantitative evaluation of amantadine in the treatment of Parkinson's disease. J Chronic Dis. Mar. 1972;25(3):149-82.
Walker, et al. Amantadine and levodopa in the treatment of Parkinson's disease. Clin Pharmacol Ther. Jan.-Feb. 1972;13(1):28-36.
Warren, et al. The use of amantadine in Parkinson's disease and other Akinetic-rigid disorders. ACNR 2004; 4(5):38-41.
Wessell, et al. NR2B selective NMDA receptor antagonist CP-101,606 prevents levodopa-induced motor response alterations in hemi-parkinsonian rats. Neuropharmacology. Aug. 2004;47(2):184-94.
Wilkinson, GR. Chapter 1: Pharmacokinetics. Goodman and Gilman's The Pharmacological Basis of Therapeutics 10$^{th}$ Ed., Hardman Limbird and Gilman Eds., McGraw-Hill, New York, 2001.
Wolf, et al. Long-term antidyskinetic efficacy of amantadine in Parkinson's disease. Mov Disord. Published online Mar. 2, 2010. [Epub ahead of print].
Yamada, el at. Changes in symptoms and plasma homovanillic acid with amantadine hydrochloride in chronic schizophrenia. Biol Psychiatry. May 15, 1997;41(10):1062-4.
U.S. Appl. No. 60/701,857, filed Jul. 22, 2005, Went et al.
U.S. Appl. No. 14/328,440, filed Jul. 10, 2014, Went et al.
U.S. Appl. No. 14/451,226, filed Aug. 4, 2014, Went et al.
U.S. Appl. No. 14/451,242, filed Aug. 4, 2014, Went et al.
U.S. Appl. No. 14/451,250, filed Aug. 4, 2014, Went et al.
U.S. Appl. No. 14/451,273, filed Aug. 4, 2014, Went et al.
U.S. Appl. No. 14/451,282, filed Aug. 4, 2014, Went et al.
CDER "Guidance for Industry Extended Release Oral Dosage Forms: Development, Evaluation, and Application of In Vitro/In Vivo Correlations" Sep. 1997, U.S. Department of Health and Human Services Food and Drug Administration, pp. 1-24.
Erkulwalter and Pillai, Southern Medical Journal, "Amantadine HCl for treatment of dementia," 79:9, Suppl. 2, 30 (1986).
Fung et al., "Drugs for Parkinson's Disease," Australian Prescriber, 24(4) (2001), pp. 92-95.
Goetz, et al. Movement Disorder Society Task Force report on the Hoehn and Yahr staging scale: status and recommendations. Mov Disord. Sep. 2004;19(9):1020-8.
Gracies JM, Olanow CW; Current and Experimental Therapeutics of Parkinson's Disease; Neuropsychopharmacology: the Fifth Generation of Progress, p. 1802; American College of Neuropsychopharmacology (2002).
Guidance for Industry. Waiver of In Vivo Bioavailability and Bioequivalence Studies for Immediate-Release Solid Oral Dosage Forms Based on a Biopharmaceutics Classification System. U.S. Department of Health and Human Services, FDA, CDER, Aug. 2000.
Guidance for Industry: Bioavailability and Bioequivalence Studies for Orally Administered Drug Products—General Considerations. U.S. Department of Health and Human Services, FDA, CDER, Mar. 2003.
Guide to MS Medications, Multiple Sclerosis Society of Canada, 2004, p. 9.
Hoffman, A. Pharmacodynamic aspects of sustained release preparations. Adv Drug Deliv Rev. Sep. 7, 1998;33(3):185-199.
International search report dated May 8, 2006 for PCT Application No. US2005/42424.
International written opinion dated Aug. 8, 2006 for PCT Application No. US2005/42780.
Jackson, Prevention and control of influenza by chemoprophylaxis and chemotherapy. Prospects from examination of recent experience. JAMA, 235(25), (1976), 2739-2742.
Notice of allowance dated Jan. 24, 2013 for U.S. Appl. No. 11/286,448.
Notice of allowance dated Jun. 4, 2014 for U.S. Appl. No. 13/958,153.
Office action dated Jan. 5, 2009 for U.S. Appl. No. 11/286,448.
Office action dated Mar. 5, 2012 for U.S. Appl. No. 11/286,448.
Office action dated Mar. 29, 2011 for U.S. Appl. No. 11/286,448.
Office action dated Apr. 16, 2013 for U.S. Appl. No. 13/756,275.
Office action dated May 20, 2014 for U.S. Appl. No. 13/958,153.
Office action dated Jul. 13, 2012 for U.S. Appl. No. 12/840,132.
Office action dated Jul. 22, 2010 for U.S. Appl. No. 11/286,448.
Office action dated Sep. 16, 2009 for U.S. Appl. No. 11/286,448.
Office action dated Nov. 20, 2013 for U.S. Appl. No. 13/958,153.
Parsons, et al. Glutamate in CNS disorders as a target for drug development: an update. Drug News Prospect. 1998;11(9):523-569.
PK-Merz® film-coated tablet, "Summary of Product Characteristics." 2003, p. 1-11.
Symmetrel. Amantadine hydrochloride. Retrieved from the internet: URL—http://www.pbs.gov.au/meds%2Fpi%2Fnvpsyrnor10611.pdf (retrieved on Jul. 25, 2012).
Toutain, et al. Bioavailability and its assessment. J Vet Pharmacol Ther. Dec. 2004;27(6):455-66.
U.S. Appl. No. 14/267,597, filed May 1, 2014, Went et al.
U.S. Appl. No. 14/523,477, filed Oct. 24, 2014, Went et al.
U.S. Appl. No. 14/523,535, filed Oct. 24, 2014, Went et al.
U.S. Appl. No. 14/523,565, filed Oct. 24, 2014, Went et al.
U.S. Appl. No. 14/523,589, filed Oct. 24, 2014, Went et al.
U.S. Appl. No. 14/523,607, filed Oct. 24, 2014, Went et al.
U.S. Appl. No. 14/523,674, filed Oct. 24, 2014, Went et al.
U.S. Appl. No. 14/523,688, filed Oct. 24, 2014, Went et al.
Hayden, et al. Comparative single-dose pharmacokinetics of amantadine hydrochloride and rimantadine hydrochloride in young and elderly adults. Antimicrob Agents Chemother. Aug. 1985;28(2):216-21.
Notice of allowance dated Oct. 9, 2014 for U.S. Appl. No. 14/328,440.
Notice of allowance dated Oct. 9, 2014 for U.S. Appl. No. 14/451,242.
Notice of allowance dated Oct. 9, 2014 for U.S. Appl. No. 14/451,250.
Notice of allowance dated Oct. 10, 2014 for U.S. Appl. No. 14/451,282.
Notice of allowance dated Oct. 14, 2014 for U.S. Appl. No. 14/451,273.
Notice of allowance dated Oct. 15, 2014 for U.S. Appl. No. 14/451,226.
Office Action dated Sep. 22, 2014 for U.S. Appl. No. 14/328,440.
Office Action dated Sep. 22, 2014 for U.S. Appl. No. 14/451,226.
Office Action dated Sep. 22, 2014 for U.S. Appl. No. 14/451,242.
Office Action dated Sep. 22, 2014 for U.S. Appl. No. 14/451,273.
Office Action dated Sep. 23, 2014 for U.S. Appl. No. 14/451,282.

Figure 1: Simulated Dissolution for TID Amantadine IR & SR

Figure 2: Simulated Plasma Concentration for TID Amantadine IR & SR over 120hrs.

Figure 3: Simulated Plasma Concentration for TID Levodopa/Carbidopa/Amantadine (IR, IR, IR) over 24hrs Figure 4: Simulated Plasma Concentration for TID Levodopa/Carbidopa/Amantadine (IR, IR, SR) over 24hrs Figure 6: Memantine, Levodopa and Carbidopa Human Pharmacokinetics
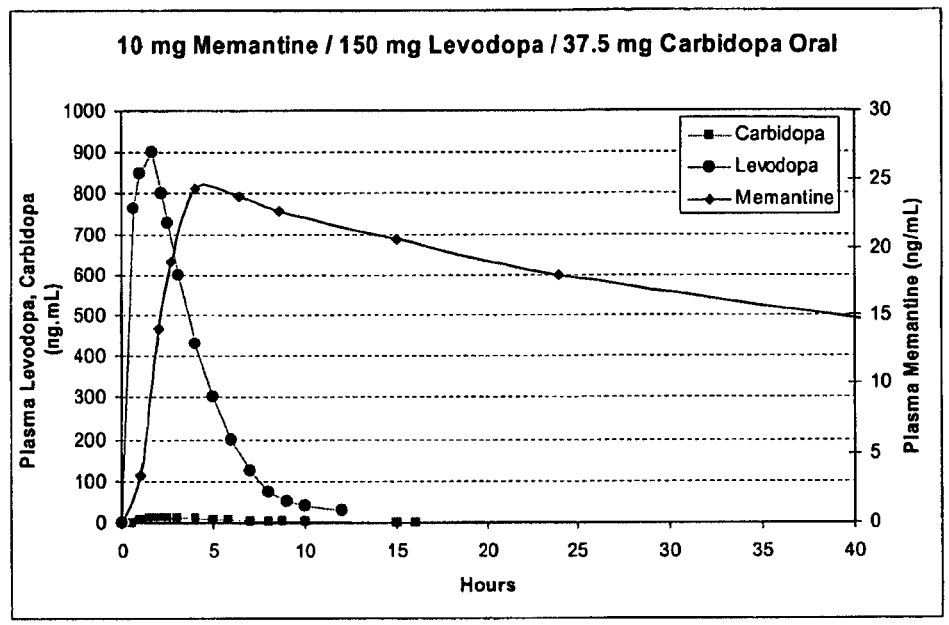
Figure 7: Target Pharmacokinetics
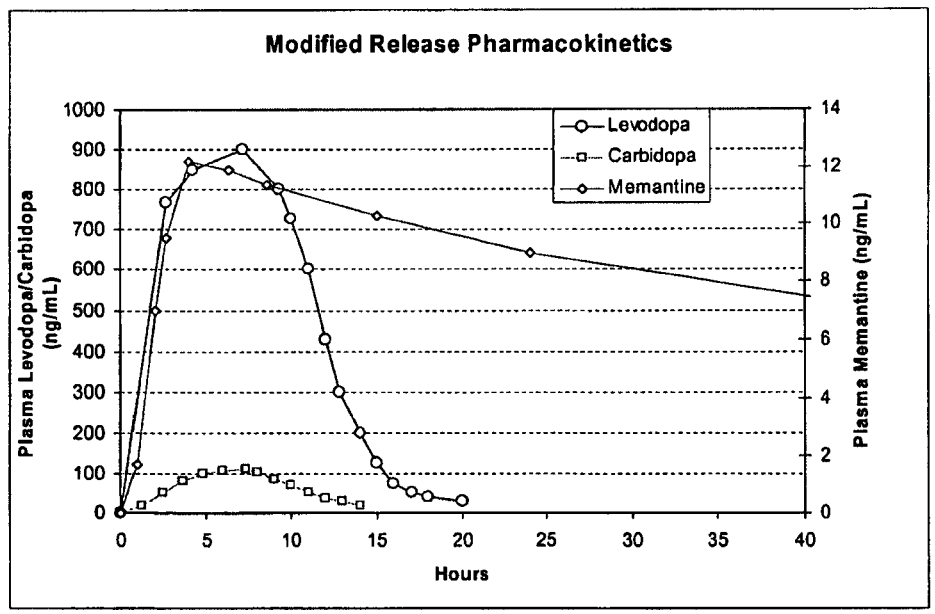

COMPOSITION AND METHOD FOR TREATING NEUROLOGICAL DISEASE

RELATED APPLICATION

This application is a continuation of U.S. patent application Ser. No. 14/328,440, filed Jul. 10, 2014, which is a continuation of U.S. patent application Ser. No. 13/958,153, filed Aug. 2, 2013, which is a continuation of U.S. patent application Ser. No. 13/756,275, filed Jan. 31, 2013, now abandoned, which is a continuation application of U.S. patent application Ser. No. 11/286,448, filed on Nov. 23, 2005, now U.S. Pat. No. 8,389,578, which claims priority to U.S. Provisional Application No. 60/631,095 filed on Nov. 24, 2004, all of which applications are incorporated herein by reference in their entirety.

FIELD OF THE INVENTION

This invention relates to compositions and methods for treating neurological diseases, such as Parkinson's disease.

BACKGROUND OF THE INVENTION

Parkinson's disease (PD) is a progressive, degenerative neurologic disorder which usually occurs in late mid-life. PD is clinically characterized by bradykinesia, tremor, and rigidity. Bradykinesia is characterized by a slowness in movement, slowing the pace of such routine activities as walking and eating. Tremor is a shakiness that generally affects limbs that are not otherwise in motion. For those PD-patients diagnosed at a relatively young age, tremor is reported as the most disabling symptom. Older patients face their greatest challenge in walking or keeping their balance. Rigidity is caused by the inability of muscles to relax as opposing muscle groups contract, causing tension which can produce aches and pains in the back, neck, shoulders, temples, or chest.

PD predominantly affects the substantia nigra (SNc) dopamine (DA) neurons and is therefore associated with a decrease in striatal DA content. Because dopamine does not cross the blood-brain barrier, PD patients may be administered a precursor, levodopa, that does cross the blood-brain barrier where it is metabolized to dopamine. Levodopa therapy is intended to compensate for reduced dopamine levels and is a widely prescribed therapeutic agent for patients with Parkinson's disease. Chronic treatment with levodopa however, is associated with various debilitating side-effects such as dyskinesia.

Since currently available drugs containing levodopa are associated with debilitating side effects, better therapies are needed for the management of PD.

SUMMARY OF THE INVENTION

In general, the present invention provides methods and compositions for treating and preventing CNS-related conditions, such as Parkinson's disease or other Parkinson's-like diseases or conditions, by administering to a subject in need thereof a combination that includes an N-Methyl-D-Aspartate receptor (NMDAr) antagonist and levodopa. Exemplary NMDAr antagonists include the aminoadamantanes, such as memantine (1-amino-3,5-dimethyladamantane), rimantadine (1-(1-aminoethyl)adamantane), or amantadine (1-amino-adamantane) as well as others described below. Because levodopa is metabolized before crossing the blood-brain barrier and has a short half-life in the circulatory system, it is typically administered in conjunction with a dopa-decarboxylase inhibitor. Examples of dopa-decarboxylase inhibitors include carbidopa, 3-hydroxy-benzylhydrazinedihydrochloride (NSD-1015), and benseraxide hydrochloride. The combination may further include a catechol-0-methyltransferase (COMT) inhibitor including, for example, talcapone and entacapone. As used herein, levodopa/carbidopa shall mean levodopa alone or in combination with a dopa-decarboxylase inhibitor such as carbidopa. Desirably, the levodopa/carbidopa is in an immediate release formulation and the NMDA receptor antagonist is in an extended release formulation. One preferred embodiment of the invention involves the combination of amantadine and levodopa/carbidopa. Desirably, amantadine is provided in an extended release formulation and levodopa/carbidopa is provided as an immediate release formulation. By combining an NMDAr antagonist (e.g., amantadine) with the second agents described herein (e.g., levodopa/carbidopa), this invention provides an effective pharmaceutical composition for treating neurological diseases such as Parkinson's disease or other Parkinson's-like diseases or conditions. The administration of this combination is postulated to maintain or enhance the efficacy of levodopa while significantly reducing its dyskinesia side effects.

The combinations described herein provide complementary benefits associated with the NMDAr antagonist or levodopa/carbidopa individually, while minimizing difficulties previously presented when each component is used separately in a patient. For example, amantadine dosing is limited by neurotoxicity that is likely associated with its short Tmax. By extending the release of amantadine, a higher effective dose can be maintained providing both dyskinesia relief and a reduction in the amount of levodopa required for treatment of the disease symptoms. Given the inherent toxicity of levodopa, such a levodopa sparing combination will result in a decline in both the dyskinesia and overall disease.

Accordingly, the pharmaceutical compositions described herein are administered so as to deliver to a subject, an amount of an NMDAr antagonist, levodopa/carbidopa or both agents that is high enough to treat symptoms or damaging effects of an underlying disease while avoiding undesirable side effects. These compositions may be employed to administer the NMDAr antagonist, the levodopa/carbidopa, or both agents at a lower frequency than presently employed, improving patient compliance, adherence, and caregiver convenience. These compositions are particularly useful as they provide the NMDAr antagonist, levodopa/carbidopa, or both agents, at a therapeutically effective amount from the onset of therapy further improving patient compliance and adherence and enable the achievement of a therapeutically effective steady-state concentration of either or both agents of the combination in a shorter period of time resulting in an earlier indication of effectiveness and increasing the utility of these therapeutic agents for diseases and conditions where time is of the essence. Also provided are methods for making and using such compositions.

The NMDAr antagonist, the levodopa/carbidopa, or both agents may be provided in a controlled or extended release form with or without an immediate release component in order to maximize the therapeutic benefit of such agents, while reducing unwanted side effects. In preferred embodiments for oral administration, levodopa/carbidopa is provided as an immediate-release formulation.

The NMDAr antagonist, the levodopa/carbidopa, or both agents may be administered in an amount similar to that typically administered to subjects. Preferably, the amount of the NMDAr antagonist may be administered in an amount greater than or less than the amount that is typically administered to subjects while the levodopa/carbidopa is provided at a lower dose than normally used. For example, the amount of amantadine required to positively affect the patient response (inclusive of adverse effects) may be 300, 400, 500, 600 mg per day rather than the typical 200-300 mg per day administered for presently approved indications i.e. without the improved formulation described herein, while the levodopa, and optionally the carbidopa, can be reduced independently by 10%, 20%, 30%, 40%, 50%, 60%, 70% or up to 80% of what is currently required in the absence of the NMDAr antagonist.

Optionally, lower or reduced amounts of both the NMDAr antagonist and the levodopa/carbidopa are used in a unit dose relative to the amount of each agent when administered independently. The present invention therefore features formulations of combinations directed to dose optimization or release modification to reduce adverse effects associated with separate administration of each agent. The combination of the NMDAr antagonist and the levodopa/carbidopa may result in an additive or synergistic response, and using the unique formulations described herein, the goal of minimizing the levodopa burden is achieved. Preferably, the NMDAr antagonist and the levodopa/carbidopa are provided in a unit dosage form.

The compositions and methods of the invention are particularly useful for the treatment of Parkinson's disease or conditions associated with Parkinson's disease. These conditions include dementia, dyskinesia, dystonia, depression, fatigue and other neuropsychiatric complications of Parkinson's disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting. All parts and percentages are by weight unless otherwise specified.

BRIEF DESCRIPTION OF THE FIGURES

FIG. 6 is a graphical representation of plasma release profiles in a human of memantine, levodopa, and carbidopa when memantine is administered separately from levodopa and carbidopa.

FIG. 7 is a graphical representation of plasma release profiles in a human of memantine, levodopa, and carbidopa when memantine, levodopa, and carbidopa are administered as part of a single controlled-release pharmaceutical composition.

DETAILED DESCRIPTION OF THE INVENTION

Figure 1:
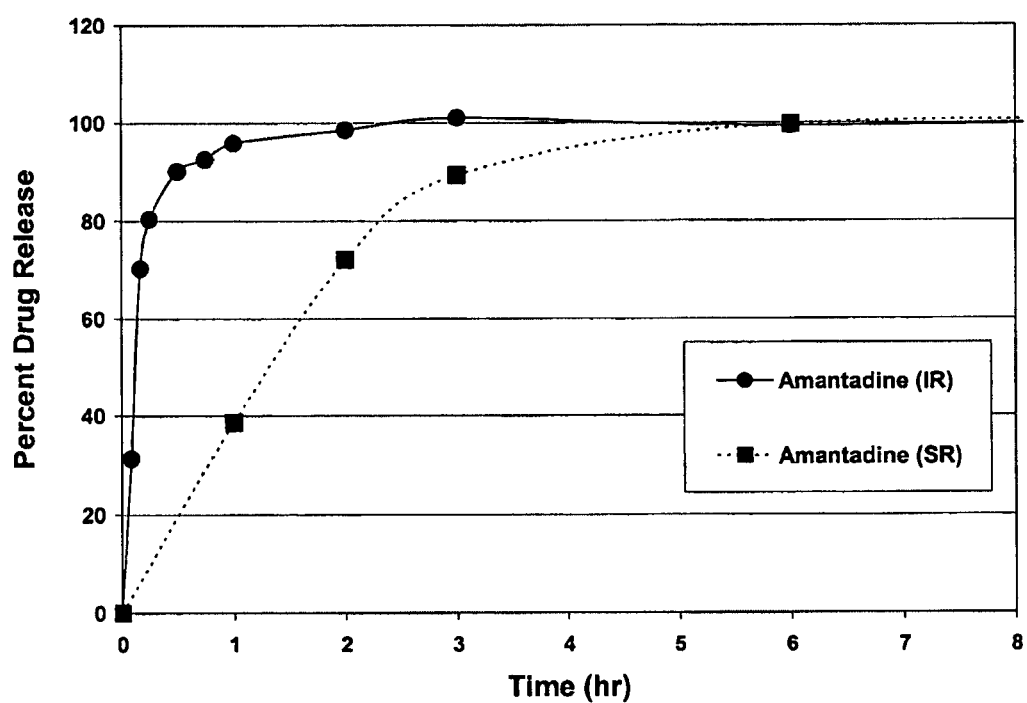
FIG. 1 is a graph showing the dissolution profiles for an immediate and sustained release formulation of amantadine. The sustained release formulation exhibits a dC/dT during the initial phase that is about 10% of that for the immediate release formulation.

In general, the present invention features pharmaceutical compositions that contain therapeutically effective levels of an NMDAr antagonist and levodopa/carbidopa and, optionally, a pharmaceutical carrier. Preferably the compositions are formulated for modified or extended release to provide a serum or plasma concentration of the NMDAr antagonist over a desired time period that is high enough to be therapeutically effective but at a rate low enough so as to avoid adverse events associated with the NMDAr antagonist. Control of drug release is particularly desirable for reducing and delaying the peak plasma level while maintaining the extent of drug bioavailability. Therapeutic levels are therefore achieved while minimizing debilitating side-effects that are usually associated with immediate release formulations. Furthermore, as a result of the delay in the time to obtain peak serum or plasma level and the extended period of time at the therapeutically effective serum or plasma level, the dosage frequency is reduced to, for example, once or twice daily dosage, thereby improving patient compliance and adherence. For example, side effects including psychosis and cognitive deficits associated with the administration of NMDAr antagonists may be lessened in severity and frequency through the use of controlled-release methods that shift the Tmax to longer times, thereby reducing the dC/dT of the drug. Reducing the dC/dT of the drug not only increases Tmax, but also reduces the drug concentration at Tmax and reduces the Cmax/Cmean ratio providing a more constant amount of drug to the subject being treated over a given period of time, enabling increased dosages for appropriate indications.

In addition, the present invention encompasses optimal ratios of NMDAr and levodopa/carbidopa, designed to not only treat the dyskinesia associated with levodopa, but also take advantage of the additivity and synergy between these drug classes. For example, the level of levodopa required to treat the disease symptoms can unexpectedly be reduced by up to 50% by the addition of 400 mg/day of amantadine.

Making NMDAr Antagonist Controlled Release Formulations

A pharmaceutical composition according to the invention is prepared by combining a desired NMDAr antagonist or antagonists with one or more additional ingredients that, when administered to a subject, causes the NMDAr antagonist to be released at a targeted rate for a specified period of time. A release profile, i.e., the extent of release of the NMDAr antagonist over a desired time, can be conveniently determined for a given time by measuring the release using a USP dissolution apparatus under controlled conditions. Preferred release profiles are those which slow the rate of uptake of the NMDAr antagonist in the neural fluids while providing therapeutically effective levels of the NMDAr antagonist.

One of ordinary skill in the art can prepare combinations with a desired release profile using the NMDAr antagonists and formulation methods described below.

NMDAr Antagonists

Any NMDAr antagonist can be used in the methods and compositions of the invention, particularly those that are nontoxic when used in the compositions of the invention. The term "nontoxic" is used in a relative sense and is intended to designate any substance that has been approved by the United States Food and Drug Administration ("FDA") for administration to humans or, in keeping with established regulatory criteria and practice, is susceptible to approval by the FDA or similar regulatory agency for any country for administration to humans or animals.

The term "NMDAr antagonist", as used herein, includes any amino-adamantane compound including, for example, memantine (1-amino-3,5-dimethyladamantane), rimantadine (1-(1-aminoethyl)adamantane), amantadine (1-amino-adamantane), as well as pharmaceutically acceptable salts thereof. Memantine is described, for example, in U.S. Pat. Nos. 3,391,142, 5,891,885, 5,919,826, and 6,187,338. Amantadine is described, for example, in U.S. Pat. Nos. 3,152,180, 5,891,885, 5,919,826, and 6,187,338. Additional aminoadamantane compounds are described, for example, in U.S. Pat. Nos. 4,346,112, 5,061,703, 5,334,618, 6,444,702, 6,620,845, and 6,662,845. All of these patents are hereby incorporated by reference.

Further NMDAr antagonists that may be employed include, for example, aminocylohexanes such as neramexane, ketamine, eliprodil, ifenprodil, dizocilpine, remacemide, iamotrigine, riluzole, aptiganel, phencyclidine, flupirtine, celfotel, felbamate, spermine, spermidine, levemopamil, dextromethorphan ((+)-3-hydroxy-N-methylmorphinan) and its metabolite, dextrorphan ((+)-3-hydroxy-N-methylmorphinan), a pharmaceutically acceptable salt, derivative, or ester thereof, or a metabolic precursor of any of the foregoing.

Optionally, the NMDAr antagonist in the instant invention is memantine and not amantadine or dextromethorphan.

Second Agents

In all foregoing aspects of the invention, the second agent is levodopa. When levodopa is in the combination, the combination preferably also includes a dopa-decarboxylase inhibitor. An example of a suitable dopa-decarboxylase inhibitor is carbidopa. Other dopa-decarboxylase inhibitors include, for example, 3-hydroxy-benzylhydrazinedihydrochloride (NSD-1015) and benseraxide hydrochloride. The combination may further include a catechol-O-methyltransferase (COMT) inhibitor including, for example, talcapone and entacapone.

Dosing, PK, & Toxicity

The NMDA receptor antagonist used in combination therapies are administered at a dosage of generally between about 1 and 5000 mg/day, between 1 and about 800 mg/day, or between 1 and 500 mg/day. For example, NMDA receptor antagonist agents may be administered at a dosage ranging between about 1 and about 500 mg/day, more preferably from about 10 to about 40, 50, 60, 70 or 80 mg/day, advantageously from about 10 to about 20 mg per day. Amantadine may be administered at a dose ranging from about 90, 100 mg/day to about 400, 500, 600, 700 or 800 mg/day, advantageously from about 100 to about 500, 600 mg per day. For example, the pharmaceutical composition may be formulated to provide memantine in an amount ranging between 1-200 mg/day, 1 and 80 mg/day, 2-80 mg/day, 10-80 mg/day, 10 and 80 mg/day, 10 and 70 mg/day, 10 and 60 mg/day, 10 and 50 mg/day, 10 and 40 mg/day, 5 and 65 mg/day, 5 and 40 mg/day, 15 and 45 mg/day, or 10 and 20 mg/day; dextromethorphan in an amount ranging between 1-5000 mg/day, 1-1000 mg/day, and 100-800 mg/day, or 200-500 mg/day. Pediatric doses will typically be lower than those determined for adults.

Table 1 shows exemplary pharmacokinetic properties (e.g., Tmax and T1/2) of memantine, amantadine, and rimantadine.

TABLE 1

Pharmacokinetics and Toxicity in humans for selected NIVIDAr antagonists

| Compound | Human PK (t½) (hours) | Tmax (hours) | Normal Dose | Dose Dependent Toxicity |
|---|---|---|---|---|
| Memantine | 60 | 3 | 10-20 mg/day, starting at 5 mg | Dose escalation required, hallucination |
| Amantadine | 15 | 3 | 100-300 mg/day, starting at 100 mg/day | Hallucination |
| Rimantadine | 25 | 6 | 100-200 mg/day | Insomnia |

When levodopa and carbidopa are both included in the composition, the levodopa dose ranges between 100 to 3000 mg per day, 75 mg and 2500 mg/day, 100-2000 mg/day, or 250 and 1000 mg/day divided for administration t.i.d. or more frequently. Carbidopa doses may range between the amounts of 1 to 1000 mg/day, 10 to 500 mg/day, and 25 to 100 mg/day. Optionally, the carbidopa is present in the combination at about 75%, 70%, 65%, 60%, 50%, 40%, 30%, 25%, 20%, and 10% of the mass of the levodopa. Alternatively, the amount of levodopa is less than 300% than the amount of carbidopa. For example, 75 mg of carbidopa (amount that is sufficient to extend the half-life of levodopa in the circulatory system) may be used in combination with 300 to 3000 mg of levodopa per day. The combination may contain a single dosage form comprising 30 to 200 mg amantadine, 30 to 250 mg levodopa, and 10 to 100 mg of carbidopa for t.i.d. or more frequent administration, including multiple dosage forms per administration.

As a result, the preferred dosage forms for optimized use are shown in Table 2 below, with their corresponding commercial equivalent.

TABLE 2

Dosage forms with and without NMDAr antagonist (amount per unit dose)

| Sinemet Compositions | | Compositions of Present Invention | | |
|---|---|---|---|---|
| Levodopa | Carbidopa | Levodopa | Carbidopa | Amantadine |
| 100 mg IR* | 25 mg IR | 50-100 mg IR | 25 mg IR | 100-200 mg IR |
| 100 mg IR | 10 mg IR | 50-100 mg IR | 10 mg IR | 50-100 mg IR |

TABLE 2-continued

Dosage forms with and without NMDAr antagonist (amount per unit dose)

| Sinemet Compositions | | Compositions of Present Invention | | |
|---|---|---|---|---|
| Levodopa | Carbidopa | Levodopa | Carbidopa | Amantadine |
| 100 mg IR | 25 mg IR | 50-100 mg IR | 25 mg IR | 100-200 mg CR** |
| 100 mg IR | 10 mg IR | 50-100 mg IR | 10 mg IR | 50-100 mg CR |

*IR: immediate release
**CR: modified release

Excipients

"Pharmaceutically or Pharmacologically Acceptable" includes molecular entities and compositions that do not produce an adverse, allergic or other untoward reaction when administered to an animal, or a human, as appropriate. "Pharmaceutically Acceptable Carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. "Pharmaceutically Acceptable Salts" include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The preparation of pharmaceutical or pharmacological compositions is known to those of skill in the art in light of the present disclosure. General techniques for formulation and administration are found in "Remington: The Science and Practice of Pharmacy, Twentieth Edition," Lippincott Williams & Wilkins, Philadelphia, Pa. Tablets, capsules, pills, powders, granules, dragees, gels, slurries, ointments, solutions suppositories, injections, inhalants and aerosols are examples of such formulations.

By way of example, modified or extended release oral formulation can be prepared using additional methods known in the art. For example, a suitable extended release form of the either active pharmaceutical ingredient or both may be a matrix tablet or capsule composition. Suitable matrix forming materials include, for example, waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are especially preferred when the active ingredients have markedly different pharmacokinetic profiles. Optionally, the finished tablet may be coated or uncoated.

The coating composition typically contains an insoluble matrix polymer (approximately 15-85% by weight of the coating composition) and a water soluble material (e.g., approximately 15-85% by weight of the coating composition). Optionally an enteric polymer (approximately 1 to 99% by weight of the coating composition) may be used or included. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups.

The coating composition may be plasticised according to the properties of the coating blend such as the glass transition temperature of the main component or mixture of components or the solvent used for applying the coating compositions. Suitable plasticisers may be added from 0 to 50% by weight of the coating composition and include, for example, diethyl phthalate, citrate esters, polyethylene glycol, glycerol, acetylated glycerides, acetylated citrate esters, dibutylsebacate, and castor oil. If desired, the coating composition may include a filler. The amount of the filler may be 1% to approximately 99% by weight based on the total weight of the coating composition and may be an insoluble material such as silicon dioxide, titanium dioxide, talc, kaolin, alumina, starch, powdered cellulose, MCC, or polacrilin potassium.

The coating composition may be applied as a solution or latex in organic solvents or aqueous solvents or mixtures thereof. If solutions are applied, the solvent may be present in amounts from approximate by 25-99% by weight based on the total weight of dissolved solids. Suitable solvents are water, lower alcohol, lower chlorinated hydrocarbons, ketones, or mixtures thereof. If latexes are applied, the solvent is present in amounts from approximately 25-97% by weight based on the quantity of polymeric material in the latex. The solvent may be predominantly water.

The NMDAr antagonist may be formulated using any of the following excipients or combinations thereof.

| Excipient name | Chemical name | Function |
|---|---|---|
| Avicel PH102 | Microcrystalline Cellulose | Filler, binder, wicking, disintegrant |
| Avicel PH101 | Microcrystalline Cellulose | Filler, binder, disintegrant |
| Eudragit RS-30D | Polymethacrylate Poly(ethyl acrylate, nethyl methacrylate, timethylammonioethyl methacrylate chloride) 1:2:0.1 | Film former, tablet binder, tablet diluent; Rate controlling polymer for controlled release |

-continued

| Excipient name | Chemical name | Function |
|---|---|---|
| Methocel K100M Premium CR | Hydroxypropyl methylcellulose | Rate controlling polymer for controlled release; binder; viscosity-increasing agent |
| Methocel K100M | Hydroxypropyl methylcellulose | Rate controlling polymer for controlled release; binder; viscosity-increasing agent |
| Magnesium Stearate | Magnesium Stearate | Lubricant |
| Talc | Talc | Dissolution control; anti-adherent, glidant |
| Triethyl Citrate | Triethyl Citrate | Plasticizer |
| Methocel E5 | Hydroxypropyl methylcellulose | Film-former |
| Opadry ® | Hydroxypropyl methylcellulose | One-step customized coating system which combines polymer, plasticizer and, if desired, pigment in a dry concentrate. |
| Surelease ® | Aqueous Ethylcellulose Dispersion | Film-forming polymer; plasticizer and stabilizers. Rate controlling polymer coating. |

The pharmaceutical composition described herein may also include a carrier such as a solvent, dispersion media, coatings, antibacterial and antifungal agents, isotonic and absorption delaying agents. The use of such media and agents for pharmaceutically active substances is well known in the art. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition may also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, may also be used as a carrier.

Methods for Preparing Modified or Extended Release Formulations

The NMDAr antagonist, the levodopa/carbidopa, or both agents may be provided in a controlled or extended release form with or without an immediate release component in order to maximize the therapeutic benefit of such agents, while reducing unwanted side effects. In the absence of modified release components (referred to herein as controlled, extended, or delayed release components), the NMDAr antagonist, levodopa/carbidopa, or both is released and transported into the body fluids over a period of minutes to several hours. The combination described herein however, may contain an NMDAr antagonist and a sustained release component, such as a coated sustained release matrix, a sustained release matrix, or a sustained release bead matrix. In one example, in addition to levodopa/carbidopa, amantadine (e.g., 50-400 mg) is formulated without an immediate release component using a polymer matrix (e.g., Eudragit), Hydroxypropyl methyl cellulose (HPMC) and a polymer coating (e.g., Eudragit). Such formulations are compressed into solid tablets or granules and coated with a controlled release material such as Opadry® or Surelease®. Levodopa/carbidopa may also be formulated as a sustained release formulation; in most cases, however, this will not be optimal.

Suitable methods for preparing the compositions described herein in which the NMDAr antagonist is provided in modified or extended release-formulations include those described in U.S. Pat. No. 4,606,909 (hereby incorporated by reference). This reference describes a controlled release multiple unit formulation in which a multiplicity of individually coated or microencapsulated units are made available upon disintegration of the formulation (e.g., pill or tablet) in the stomach of the subject (see, for example, column 3, line 26 through column 5, line 10 and column 6, line 29 through column 9, line 16). Each of these individually coated or microencapsulated units contains cross-sectionally substantially homogenous cores containing particles of a sparingly soluble active substance, the cores being coated with a coating that is substantially resistant to gastric conditions but which is erodable under the conditions prevailing in the gastrointestinal tract.

The composition of the invention may alternatively be formulated using the methods disclosed in U.S. Pat. No. 4,769,027, for example. Accordingly, extended release formulations involve prills of pharmaceutically acceptable material (e.g., sugar/starch, salts, and waxes) may be coated with a water permeable polymeric matrix containing an NMDAr antagonist and next overcoated with a water-permeable film containing dispersed within it a water soluble particulate pore forming material.

The NMDAr antagonist composition may additionally be prepared as described in U.S. Pat. No. 4,897,268, involving a biocompatible, biodegradable microcapsule delivery system. Thus, the NMDAr antagonist may be formulated as a composition containing a blend of free-flowing spherical particles obtained by individually microencapsulating quantities of memantine, for example, in different copolymer excipients which biodegrade at different rates, therefore releasing memantine into the circulation at a predetermined rates. A quantity of these particles may be of such a copolymer excipient that the core active ingredient is released quickly after administration, and thereby delivers the active ingredient for an initial period. A second quantity of the particles is of such type excipient that delivery of the encapsulated ingredient begins as the first quantity's delivery begins to decline. A third quantity of ingredient may be encapsulated with a still different excipient which results in delivery beginning as the delivery of the second quantity beings to decline. The rate of delivery may be altered, for example, by varying the lactide/glycolide ratio in a poly(D,L-lactide-co-glycolide) encapsulation. Other polymers that may be used include polyacetal polymers, polyorthoesters, polyesteramides, polycaprolactone and copolymers thereof, polycarbonates, polyhydroxybuterate and copolymers thereof, polymaleamides, copolyaxalates and polysaccharides.

Alternatively, the composition may be prepared as described in U.S. Pat. No. 5,395,626, which features a multilayered controlled release pharmaceutical dosage form. The dosage form contains a plurality of coated particles wherein each has multiple layers about a core containing an NMDAr antagonist whereby the drug containing core and at least one other layer of drug active is overcoated with a controlled release barrier layer therefore providing at least two controlled releasing layers of a water soluble drug from the multilayered coated particle Release Profile The compositions described herein are formulated such that the NMDAr antagonist, levodopa/carbidopa, or both agents have an in vitro dissolution profile that is equal to or slower than that for an immediate release formulation. As used herein, the immediate release (IR) formulation for memantine means the present commercially available 5 mg and 10 mg tablets (i.e., Namenda from Forest Laboratories, Inc. or formulations having substantially the same release profiles as Namenda); and the immediate release (IR) formulation of amantadine means the present commercially available 100 mg tablets (i.e., Symmetrel from Endo Pharmaceuticals, Inc. or formulations having substantially the same release profiles as Symmetrel); and the immediate release (IR) formulation of levodopa/carbidopa means the present commercially available 25 mg/100 mg, 10 mg/100 mg, 25 mg/250 mg tablets of carbidopa/levodopa (i.e., Sinemet from Merck & Co. Inc. or formulations having substantially the same release profiles as Sinemet). These compositions may comprise immediate release, sustained or extended release, or delayed release components, or may include combinations of same to produce release profiles such that the fraction of NMDAr antagonist or levodopa/carbidopa released is greater or equal to 0.01 $(0.297+0.0153*e^{(0.515*t)})$ and less than or equal to $1-e^{(-10.9*t)}$ as measured using a USP type 2 (paddle) dissolution system at 50 rpm, at a temperature of 37±0.5° C., in water, where t is the time in hours and t is greater than zero and equal or less than 17. Thus, the fraction of NMDAr antagonist or levodopa/carbidopa released is less than 93% in 15 minutes and 7.7%-100% in 12 hours using a USP type 2 (paddle) dissolution system at 50 rpm, at a temperature of 37±0.5° C. in a neutral pH (e.g. water or buffered aqueous solution) or acidic (e.g. 0.1N HCl) dissolution medium. Optionally, the fraction of released NMDAr antagonist or levodopa/carbidopa is greater than or equal to 0.01 $(0.297+0.0153*e^{(0.515*t)})$, and less than or equal to $1-e^{(-0.972*t)}$ as measured using a USP type 2 (paddle) dissolution system at 50 rpm, at a temperature of 37±0.5° C., in water, where t is the time in hours and t is greater than zero and equal or less than 17. Thus, the fraction of NMDAr antagonist or levodopa/carbidopa that is released may range between 0.1%-62% in one hour, 0.2%-86% in two hours, 0.6%-100% in six hours, 2.9%-100% in 10 hours, and 7.7%-100% in 12 hours using a USP type 2 (paddle) dissolution system at 50 rpm, at a temperature of 37±0.5° C. in a neutral pH (e.g. water or buffered aqueous solution) or acidic (e.g. 0.1 N HCl) dissolution medium. Optionally, the NMDA receptor antagonist has a release profile ranging between 0.1%-20% in one hour, 5%-30% in two hours, 40%-80% in six hours, 70% or greater (e.g., 70%-90%) in 10 hours, and 90% or greater (e.g., 90-95%) in 12 hours as measured in a dissolution media having a neutral pH (e.g. water or buffered aqueous solution) or in an acidic (e.g. 0.1 N HCl) dissolution medium. For example, a formulation containing amantadine may have a release profile ranging between 0-60% or 0.1-20% in one hour, 0-86% or 5-30% at two hours, 0.6-100% or 40-80% at six hours, 3-100% or 50% or more (e.g., 50-90%) at ten hours, and 7.7-100% at twelve hours in a dissolution media having a neutral pH (e.g. water or buffered aqueous solution) or in an acidic (e.g. 0.1 N HCl) dissolution medium. In one embodiment, the NMDAr antagonist, the levodopa/carbidopa, or both agents have an in vitro dissolution profile of less than 25%, 15%, 10%, or 5% in fifteen minutes; 50%, 30%, 25%, 20%, 15%, or 10% in 30 minutes and more than 60%, 65% 70%, 75%, 80%, 85%, 90%, 95% at 16 hours as obtained using a USP type II (paddle) dissolution system at 50 rpm, at a temperature of 37±0.5° C. in water. Desirably, the NMDAr antagonist, the levodopa/carbidopa, or both agents has a dissolution of at least 65%, 70%, 75%, 80%, 85%, 90%, or 95% in a dissolution media having a pH of 1.2 at 10 hours. It is important to note that the dissolution profile for the NMDAr antagonist may be different than the release profile for levodopa/carbidopa. In a preferred embodiment, the levodopa/carbidopa release profile is equal to or similar to that for an immediate release formulation and the release profile for the NMDAr antagonist is controlled to provide a dissolution profile of less than 30% in one hour, less than 50% in two hours, and greater than 95% in twelve hours using a USP type II (paddle) dissolution system at 50 rpm, at a temperature of 37±0.5° C. in water.

Figure 2:
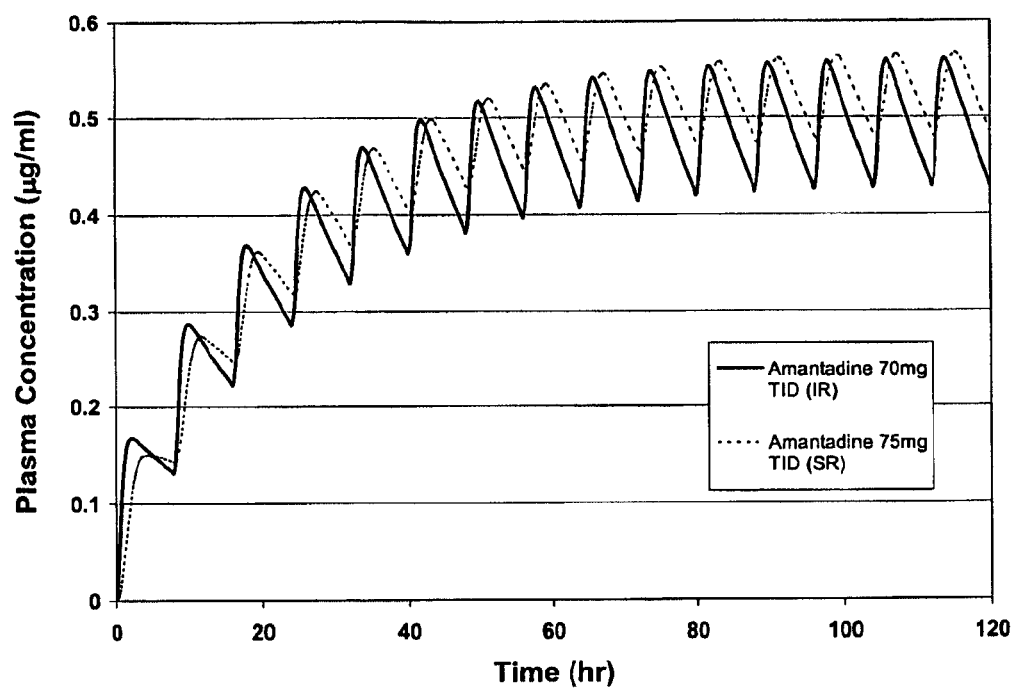
FIG. 2 is a graph showing the amantadine plasma concentration over a period of 5 days, as predicted by Gastro-Plus software package v.4.0.2, following the administration of either 70 mg amantadine in an immediate release formulation t.i.d. or 75 mg amantadine in a sustained release formulation t.i.d. The sustained release formulation peaks are similar in height to the immediate release formulation even with a higher administered dose and the diurnal variation is substantially reduced.
Figure 3:
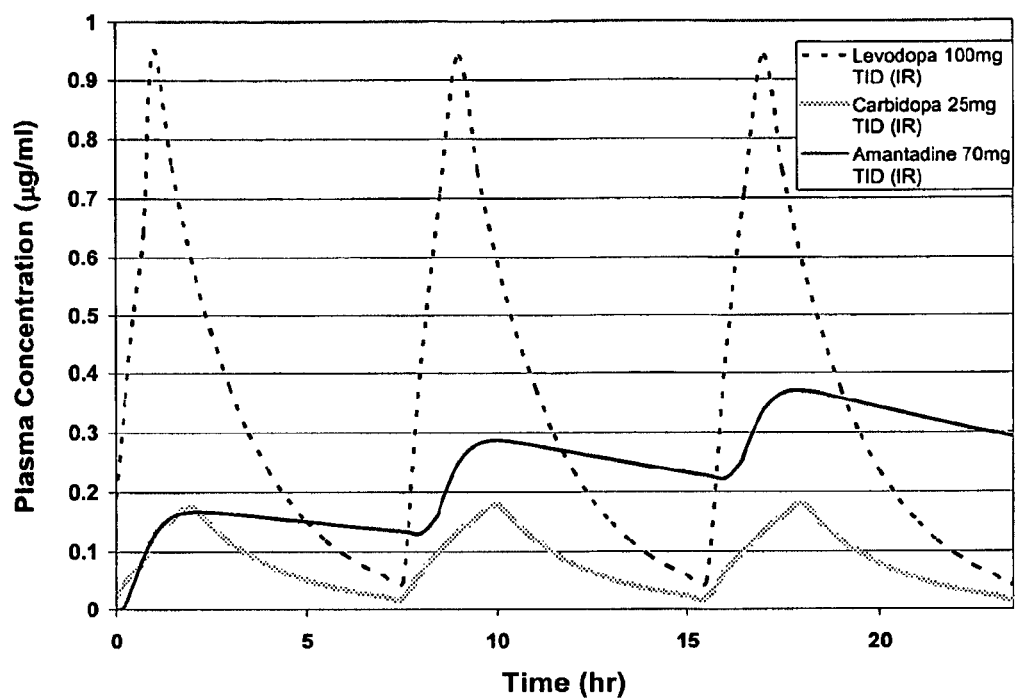
FIG. 3 is a graph showing the plasma profiles simulated using Gastro-Plus for t.i.d. administration of amantadine (70 mg), levodopa (100 mg), and carbidopa (25 mg), all in an immediate release form.
Figure 4:
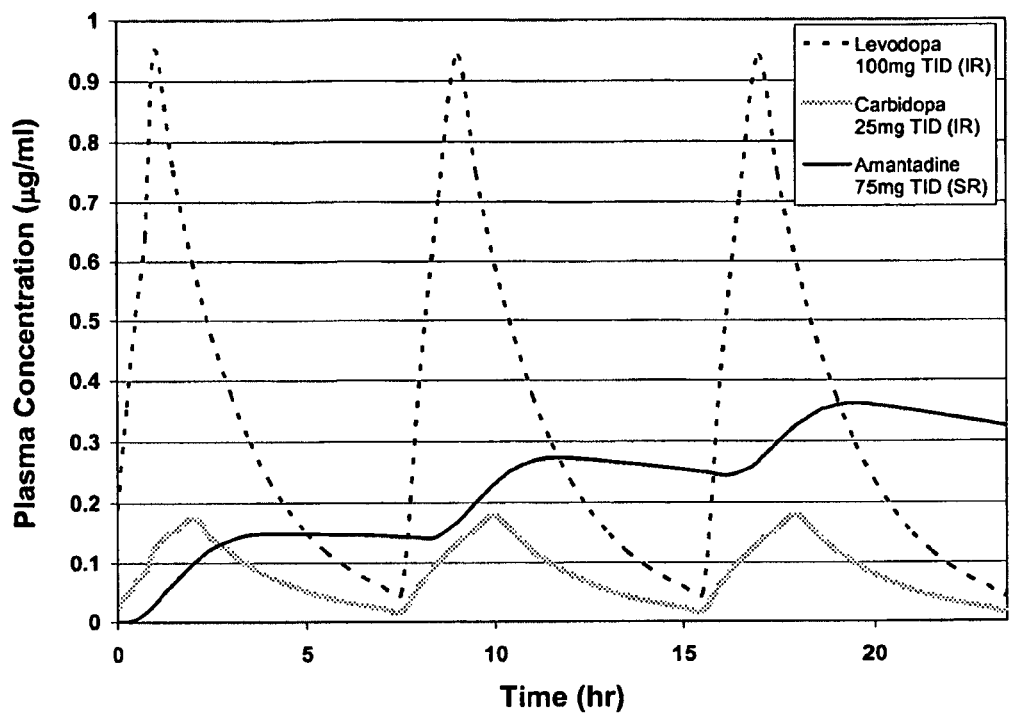
FIG. 4 is a graph showing the plasma profiles simulated using Gastro-Plus for t.i.d. administration of amantadine (75 mg), levodopa (100 mg), and carbidopa (25 mg), where the amantadine is in a sustained release form and the levodopa and carbidopa are in an immediate release form.
Figure 5:
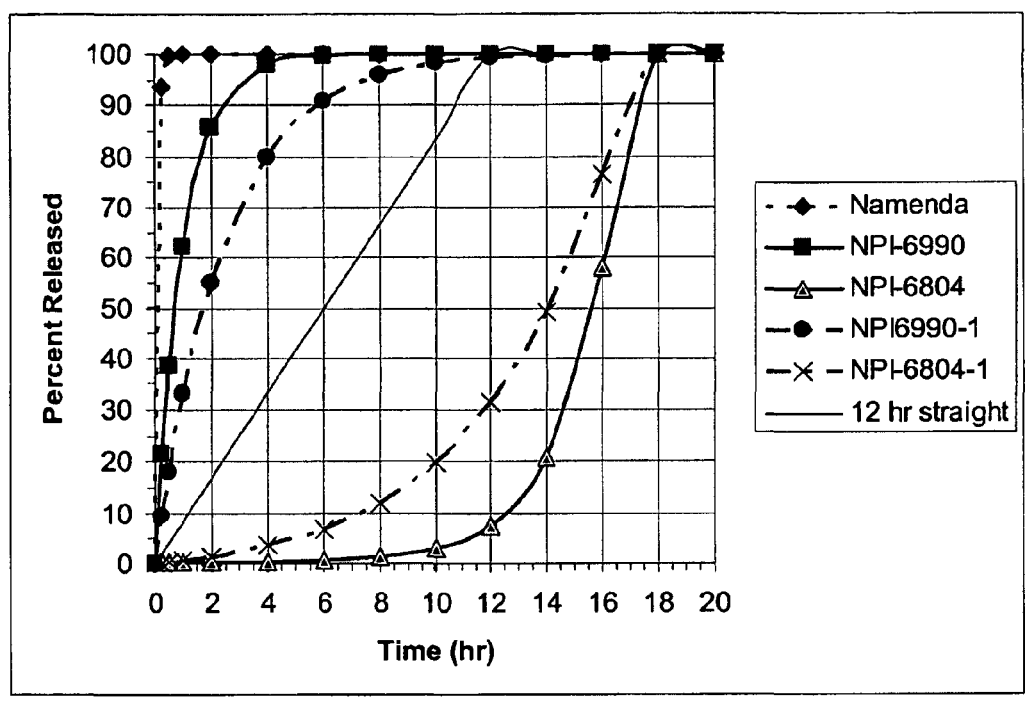
FIG. 5 is a graph representing dissolution profiles for various aminoadamantane formulations including an immediate release form of the NMDAr antagonist memantine (Namenda).

Desirably, the compositions described herein have an in vitro profile that is substantially identical to the dissolution profile shown in FIG. 5 and, upon administration to a subject at a substantially constant daily dose, achieves a serum concentration profile that is substantially identical to that shown in FIGS. 2 and 4.

As described above, the NMDAr antagonist, the levodopa/carbidopa, or both agents may be provided in a modified or extended release form. Modified or extended drug release is generally controlled either by diffusion through a coating or matrix or by erosion of a coating or matrix by a process dependent on, for example, enzymes or pH. The NMDAr antagonist or the levodopa/carbidopa may be formulated for modified or extended release as described herein or using standard techniques in the art. In one example, at least 50%, 75%, 90%, 95%, 96%, 97%, 98%, 99%, or even in excess of 99% of the NMDAr antagonist or the levodopa/carbidopa is provided in an extended release dosage form. In a preferred embodiment, the levodopa/carbidopa is provided in an immediate release formulation and the NMDAr antagonist is in either an immediate or modified release form.

The composition described herein is formulated such the NMDAr antagonist or levodopa/carbidopa has an in vitro dissolution profile ranging between 0.1%-20% in one hour, 5%-30% in two hours, 40%-80% in six hours, 50%-90% in 10 hours, and 90%-95% in 12 hours using a USP type 2 (paddle) dissolution system at 50 rpm, at a temperature of 37±0.5° C. using 0.1N HCl as a dissolution medium. Alternatively, the NMDAr antagonist has an in vitro dissolution profile in a solution with a neutral pH (e.g., water) that is substantially the same as its dissolution profile in an acidic dissolution medium. Thus, the NMDAr antagonist may be released in both dissolution media at the following rate: between 0.1-20% in one hour, 5-30% in two hours, 40-80% in six hours, 70-90% in 10 hours, and 90%-95% in 12 hours as obtained using a USP type 2 (paddle) dissolution system at 50 rpm, at a temperature of 37±0.5° C. In one embodiment, the NMDAr antagonist has an in vitro dissolution profile of less than 15%, 10%, or 5% in fifteen minutes, 25%, 20%, 15%, or 10% in 30 minutes, and more than 60% at 16 hours as obtained using a USP type II (paddle) dissolution system at 50 rpm, at a temperature of 37±0.5° C. in water. Desirably, the NMDAr antagonist has a dissolution of at least 65%, 70%, 75%, 80%, 85%, 90%, or 95% at 10 hours in a dissolution medium having a pH of 1.2.

Initial Rate In Vivo, Delayed Tmax

As used herein, "C" refers to the concentration of an active pharmaceutical ingredient in a biological sample, such as a patient sample (e.g. blood, serum, and cerebrospinal fluid). The time required to reach the maximal concentration ("Cmax") in a particular patient sample type is referred to as the "Tmax". The change in concentration is termed "dC" and the change over a prescribed time is "dC/dT".

The NMDAr antagonist or levodopa/carbidopa is provided as a sustained release formulation that may or may not contain an immediate release formulation. If desired, the NMDAr antagonist may be formulated so that it is released at a rate that is significantly reduced over an immediate release (IR) dosage form, with an associated delay in the Tmax. The pharmaceutical composition may be formulated to provide a shift in Tmax by 24 hours, 16 hours, 8 hours, 4 hours, 2 hours, or at least 1 hour. The associated reduction in dC/dT may be by a factor of approximately 0.05, 0.10, 0.25, 0.5 or at least 0.8. In addition, the NMDAr antagonist levodopa/carbidopa may be provided such that it is released at a rate resulting in a Cmax/Cmean of approximately 2 or less for approximately 2 hours to at least 8 hours after the NMDAr antagonist is introduced into a subject. Optionally, the sustained release formulations exhibit plasma concentration curves having initial (e.g., from 0, 1, 2 hours after administration to 4, 6, 8 hours after administration) slopes less than 75%, 50%, 40%, 30%, 20% or 10% of those for an IR formulation of the same dosage of the same NMDAr antagonist. The precise slope for a given individual will vary according to the NMDAr antagonist being used or other factors, including whether the patient has eaten or not. For other doses, e.g., those mentioned above, the slopes vary directly in relationship to dose. The determination of initial slopes of plasma concentration is described, for example, by U.S. Pat. No. 6,913,768, hereby incorporated by reference.

Desirably, the NMDAr antagonist or the levodopa/carbidopa is released into a subject sample at a slower rate than observed for an immediate release (IR) formulation of the same quantity of the antagonist, such that the rate of change in the biological sample measured as the dC/dT over a defined period within the period of 0 to Tmax for the IR formulation (e.g., Namenda, a commercially available IR formulation of memantine). In some embodiments, the dC/dT rate is less than about 80%, 70%, 60%, 50%, 40%, 30%, 20%, or 10% of the rate for the IR formulation. In some embodiments, the dC/dT rate is less than about 60%, 50%, 40%, 30%, 20%, or 10% of the rate for the IR formulation. Similarly, the rate of release of the NMDAr antagonist or the levodopa/carbidopa from the present invention as measured in dissolution studies is less than 80%, 70%, 60% 50%, 40%, 30%, 20%, or 10% of the rate for an IR formulation of the same NMDAr antagonist or levodopa/carbidopa over the first 1, 2, 4, 6, 8, 10, or 12 hours.

In a preferred embodiment, the dosage form is provided in a non-dose escalating, three times per day (t.i.d.) form. In preferred embodiments, the concentration ramp (or Tmax effect) may be reduced so that the change in concentration as a function of time (dC/dT) is altered to reduce or eliminate the need to dose escalate the NMDAr antagonist. A reduction in dC/dT may be accomplished, for example, by increasing the Tmax in a relatively proportional manner. Accordingly, a two-fold increase in the Tmax value may reduce dC/dT by approximately a factor of 2. Thus, the NMDAr antagonist may be provided so that it is released at a rate that is significantly reduced over an immediate release (IR) dosage form, with an associated delay in the Tmax. The pharmaceutical composition may be formulated to provide a shift in Tmax by 24 hours, 16 hours, 8 hours, 4 hours, 2 hours, or at least 1 hour. The associated reduction in dC/dT may be by a factor of approximately 0.05, 0.10, 0.25, 0.5 or at least 0.8. In certain embodiments, this is accomplished by releasing less than 30%, 50%, 75%, 90%, or 95% of the NMDAr antagonist into the circulatory or neural system within one hour of such administration.

The concentration ramp for levodopa/carbidopa may also be reduced, however such changes will not be preferred in most oral formulations due to the marked reduction in absorption of levodopa/carbidopa after it passes the duodenal region of the gastrointestinal tract.

Optionally, the modified release formulations exhibit plasma concentration curves having initial (e.g., from -2 hours after administration to 4 hours after administration) slopes less-than 75%, 50%, 40%, 30%, 20% or 10% of those for an IR formulation of the same dosage of the same NMDAr antagonist or levodopa/carbidopa. The precise slope for a given individual will vary according to the NMDAr antagonist or levodopa/carbidopa being used, the quantity delivered, or other factors, including, for some active pharmaceutical agents, whether the patient has eaten or not. For other doses, e.g., those mentioned above, the slopes vary directly in relationship to dose.

Using the sustained release formulations or administration methods described herein, the NMDAr antagonist reaches a therapeutically effective steady state plasma concentration in a subject within the course of the first two, three, five, seven, nine, ten, twelve, fifteen, or twenty days of administration. For example, the formulations described herein, when administered at a substantially constant daily dose (e.g., at a dose ranging between 200 mg and 800 mg, preferably between 200 mg and 600 mg, and more preferably between 200 mg and 400 mg per day) may reach a steady state plasma concentration in approximately 70%, 60%, 50%, 40%, 30%, or less of the time required to reach such plasma concentration when using a dose escalating regimen.

Dosing Frequency and Dose Escalation

According to the present invention, a subject (e.g., human) having or at risk of having such conditions is administered any of the compositions described herein (e.g., three times per day (t.i.d.), twice per day (b.i.d.), or once per day (q.d.)). While immediate release formulations of NMDAr antagonists are typically administered in a dose-escalating fashion, the compositions described herein may be essentially administered at a constant, therapeutically-effective dose from the onset of therapy. For example, a composition containing a sustained release formulation of amantadine may be administered three times per day, twice per day, or once per day in a unit dose comprising a total daily amantadine dose of 100 mg, 200 mg, 300 mg, 400 mg, 500 mg, 600 mg, 700 mg, or 800 mg. In embodiments comprising a single dosage form containing an NMDAr antagonist and levodopa/carbidopa wherein the levodopa/carbidopa is in an immediate release form, the dosing frequency will be chosen according to the levodopa/carbidopa requirements, (e.g. three times per day).

Reduced Time to Therapeutic Concentration and Efficacy

Immediate release (IR) formulations of memantine (e.g., Namenda) are typically administered at low doses (e.g., 5 mg/day) and are progressively administered at increasing frequency and dose over time to reach a steady state serum concentration that is therapeutically effective. According to the manufacturer's FDA approved label, Namenda, an immediate release (IR) formulation of memantine, is first administered to subjects at a dose of 5 mg per day. After an acclimation period of typically one week, subjects are administered with this dose twice per day. Subjects are next administered with a 5 mg and 10 mg dosing per day and finally administered with 10 mg Namenda twice daily. Using this dosing regimen, a therapeutically effective steady state serum concentration may be achieved within 30 days of the onset of therapy. Using a modified release formulation comprising (22.5 mg memantine,) however, a therapeutically effective steady state concentration may be achieved substantially sooner (within about 13 days), without using a dose escalating regimen. Furthermore, the slope during each absorption period for the sustained release formulation is less (i.e. not as steep) as the slope for Namenda. Accordingly, the dC/dT of the sustained release formulation is reduced relative to the immediate release formulation even though the dose administered is larger than for the immediate release formulation. Based on this model, a sustained release formulation of an NMDAr antagonist may be administered to a subject in an amount that is approximately the full strength dose (or that effectively reaches a therapeutically effective dose) from the onset of therapy and throughout the duration of treatment. Accordingly, a dose escalation would not be required.

Treatment of a subject with the subject of the present invention may be monitored using methods known in the art. The efficacy of treatment using the composition is preferably evaluated by examining the subject's symptoms in a quantitative way, e.g., by noting a decrease in the frequency or severity of symptoms or damaging effects of the condition, or an increase in the time for sustained worsening of symptoms. In a successful treatment, the subject's status will have improved (i.e., frequency or severity of symptoms or damaging effects will have decreased, or the time to sustained progression will have increased). In the model described in the previous paragraph, the steady state (and effective) concentration of the NMDAr antagonist is reached in 25%, 40%, 50%, 60%, 70%, 75%, or 80% less time than in the dose escalated approach.

In another embodiment, a composition is prepared using the methods described herein, wherein such composition comprises memantine or amantadine and a release modifying excipient, wherein the excipient is present in an amount sufficient to ameliorate or reduce the dose-dependent toxicity associated with the memantine or amantadine relative to an immediate release (IR) formulation of memantine, such as Namenda, or amantadine, such as Symmetrel. The use of these compositions enables safer administration of these agents, and even permits the safe use of higher levels for appropriate indications, beyond the useful range for the presently available versions of memantine (5 mg and 10 mg per dose to 20 mg per day) and amantadine (100 mg to 300 mg per day with escalation).

Indications Suitable for Treatment

The compositions and methods of the present invention are particularly suitable for the treatment of Parkinson's disease or conditions associated with Parkinson's disease. These conditions include dementia, dyskinesia, dystonia, depression, fatigue and other neuropsychiatric complications of Parkinson's disease.

Formulations for Alternate Specific Routes of Administration

The pharmaceutical compositions may be optimized for particular types of delivery. For example, pharmaceutical compositions for oral delivery are formulated using pharmaceutically acceptable carriers that are well known in the art. The carriers enable the agents in the composition to be formulated, for example, as a tablet, pill, capsule, solution, suspension, sustained release formulation; powder, liquid or gel for oral ingestion by the subject.

The NMDAr antagonist may also be delivered in an aerosol spray preparation from a pressurized pack, a nebulizer or from a dry powder inhaler. Suitable propellants that can be used in a nebulizer include, for example, dichlorodifluoromethane, trichlorofluoromethane, dichlorotetrafluoroethane and carbon dioxide. The dosage can be determined by providing a valve to deliver a regulated amount of the compound in the case of a pressurized aerosol.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

In some embodiments, for example, the composition may be delivered intranasally to the cribriform plate rather than by inhalation to enable transfer of the active agents through the olfactory passages into the CNS and reducing the systemic administration. Devices commonly used for this route of administration are included in U.S. Pat. No. 6,715,485. Compositions delivered via this route may enable increased CNS dosing or reduced total body burden reducing systemic toxicity risks associated with certain drugs.

Additional formulations suitable for other modes of administration include rectal capsules or suppositories. For suppositories, traditional binders and carriers may include, for example, polyalkylene glycols or triglycerides; such suppositories may be formed from mixtures containing the active ingredient in the range of 0.5% to 10%, preferably 1%-2%.

The composition may optionally be formulated for delivery in a vessel that provides for continuous long-term delivery, e.g., for delivery up to 30 days, 60 days, 90 days, 180 days, or one year. For example the vessel can be provided in a biocompatible material such as titanium. Long-term delivery formulations are particularly useful in subjects with chronic conditions, for assuring improved patient compliance, and for enhancing the stability of the compositions.

Optionally, the NMDA receptor antagonist, levodopa/carbidopa, or both is prepared using the OROS® technology, described for example, in U.S. Pat. Nos. 6,919,373, 6,923, 800, 6,929,803, 6,939,556, and 6,930,128, all of which are hereby incorporated by reference. This technology employs osmosis to provide precise, controlled drug delivery for up to 24 hours and can be used with a range of compounds, including poorly soluble or highly soluble drugs. OROS® technology can be used to deliver high drug doses meeting high drug loading requirements. By targeting specific areas of the gastrointestinal tract, OROS® technology may provide more efficient drug absorption and enhanced bioavailability. The osmotic driving force of OROS® and protection of the drug until the time of release eliminate the variability of drug absorption and metabolism often caused by gastric pH and motility.

Formulations for continuous long-term delivery are provided in, e.g., U.S. Pat. Nos. 6,797,283; 6,764,697; 6,635, 268, and 6,648,083.

If desired, the components may be provided in a kit. The kit can additionally include instructions for using the kit.

Additional Methods for Making Modified Release Formulations

Additional methods for making modified release formulations are described in, e.g., U.S. Pat. Nos. 5,422,123, 5,601, 845, 5,912,013, and 6,194,000, all of which are hereby incorporated by reference.

In some embodiments, for example, the composition may be delivered via intranasal, buccal, or sublingual routes to the brain rather than by inhalation to enable transfer of the active agents through the olfactory passages into the CNS and reducing the systemic administration. Devices commonly used for this route of administration are included in U.S. Pat. No. 6,715,485. Compositions delivered via this route may enable increased CNS dosing or reduced total body burden reducing systemic toxicity risks associated with certain drugs.

Preparation of a pharmaceutical composition for delivery in a subdermally implantable device can be performed using methods known in the art, such as those described in, e.g., U.S. Pat. Nos. 3,992,518; 5,660,848; and 5,756,115.

The invention will be illustrated in the following non-limiting examples.

EXAMPLES

Example 1

Measuring Release Profiles In Vitro

Compositions containing an aminoadamantane and levodopa/carbidopa are analyzed for release of the aminoadamantane and levodopa/carbidopa, according to the USP type 2 apparatus at a speed of 50 rpm. The dissolution media used include water, 0.1N HCl, or 0.1N HCl adjusted to pH 6.8 at 2 hours with phosphate buffer. The dissolution medium is equilibrated to 37±0.5° C.

The USP reference assay method for amantadine is used to measure the fraction of memantine released from the compositions prepared herein. Briefly, 0.6 mL sample (from the dissolution apparatus at a given time point) is placed into a 15 mL culture tube. 1.6 mL 0.1% Bromocresol Purple (in acetic acid) is added and vortexed for five seconds. The mixture is allowed to stand for approximately five minutes. 3 mL Chloroform is added and vortexed for five seconds. The solution is next centrifuged (speed 50 rpm) for five minutes. The top layer is removed with a disposable pipette. A sample is drawn into 1 cm flow cell and the absorbance is measured at 408 nm at 37° C. and compared against a standard curve prepared with known quantities of the same aminoadamantane. The quantity of determined is plotted against the dissolution time for the sample.

The USP reference assay method for levodopa is used to measure the fraction of levodopa released from the compositions prepared herein. Briefly, 0.5 ml samples from the dissolution apparatus removed at various times are assayed by liquid chromatography. The chromatograph is equipped with a 280 nm detector and a 3.9 mm×30 cm column containing packing L1. The mobile phase is 0.09 N sodium phosphate, 1 mM sodium 1-decanesulfonate, pH 2.8. With the flow rate adjusted to about 2 mL per minute, the levodopa elutes in about 4 minutes and carbidopa elutes in about 11 minutes. From the saved dissolution samples, a 0.02 ml aliquot is injected into the chromatograph and the absorbance is measure and compared to standard to determine concentration & quantity. The quantity dissolved is then plotted against the dissolution time for the sample.

Example 2

Preparation of Amantadine Extended Release Capsules

Amantadine extended release capsules may be formulated as follows or as described, for example, in U.S. Pat. No. 5,395,626.

A. Composition: Unit Dose

The theoretical quantitative composition (per unit dose) for amantadine extended release capsules is provided below.

| Component | % weight/weight | mg/Capsule |
|---|---|---|
| Amantadine | 68.34 | 200.00 |
| OPADRY ® Clear YS-3-7011 [1] (Colorcon, Westpoint, PA) | 1.14 | 5.01 |
| Purified Water, USP [2] | — | — |
| Sugar Spheres, NF | 12.50 | 54.87 |
| OPADRY ® Clear YS-1-7006 [3] (Colorcon, Westpoint, PA) | 4.48 | 19.66 |
| SURELEASE ® E-7-7050 [4] (Colorcon, Westpoint, PA) | 13.54 | 59.44 |
| Capsules [5] | — | — |
| TOTAL. | 100.00% | 338.98 mg [6] |

[1] A mixture of hydroxypropyl methylcellulose, polyethylene glycol, propylene glycol.
[2] Purified Water, USP is evaporated during processing.
[3] A mixture of hydroxypropyl methylcellulose and polyethylene glycol
[4] Solid content only of a 25% aqueous dispersion of a mixture of ethyl cellulose, dibutyl sebacate, oleic acid, ammoniated water and fumed silica. The water in the dispersion is evaporated during processing.
[5] White, opaque, hard gelatin capsule, size 00.
[6] Each batch is assayed prior to filling and the capsule weight is adjusted as required to attain 200 mg amantadine per capsule.

The quantitative batch composition for amantadine extended release capsule is shown below. (Theoretical batch quantity 25,741 capsules).

Step 1: Prep of Amantadine HCl Beads (Bead Build-up #1)

| Component | Weight (kg) |
|---|---|
| Amantadine | 12.000 |
| OPADRY ® Clear YS-3-7011 | 0.200 |
| Purified Water, USP | 5.454 |
| Sugar Sphere, NF | 4.000 |
| Total Weight Amantadine Beads | 16.200 kg |

The amantadine beads obtained from step 1 are used as follows.

Step 2: Clear & Sustained Release Bead Coating #1

| Component | Weight (kg) |
|---|---|
| Amantadine Beads | 8.000 |
| OPADRY ® Clear YS-1-7006 | 0.360 |
| Purified Water, USP | 5.928 |
| Surelease ® E-7-7050 | 0.672 |
| Total Weight Clear Coated Sustained Release Beads | 9.032 kg |

The sustained release beads obtained from step 2 are used as follows.

Step 3: Amantadine HCl Beads (Build-up #2)

| Component | Weight (kg) |
|---|---|
| Sustained Release Beads | 8.000 |
| Amantadine | 4.320 |
| OPADRY ® Clear YS-3-7011 | 0.072 |
| Purified Water, USP | 1.964 |
| Total Weight Amantadine Beads | 12.392 kg |

The amantadine beads obtained from step 3 are formulated as follows.

Step 4: Clear & Sustained Release Bead Coating #2

| Component | Weight (kg) |
|---|---|
| Amantadine Beads | 10.000 |
| OPADRY ® Clear YS-1-7006 | 0.250 |
| Purified Water, USP | 6.450 |

-continued

| Component | Weight (kg) |
|---|---|
| Surelease ® E-7-7050 | 1.050 |
| Total Weight Amantadine Extended Release Beads | 11.300 kg |

Step 5: Capsule Filling—Gelatin Capsules, Size 00, are Filled with 339 mg of the Amantadine Beads Prepared in Step 4.

Example 3

Extended Release Amantadine Formulation with Immediate Release Carbidopa and Levodopa Levodopa and Carbidopa are formulated into pellets suitable for filling, yet having an immediate release profile. (see, for example, U.S. Pat. No. 5,912,013).

Levodopa Plus Carbidopa Core Pellets

|  | Weight Percent | Kilograms |
|---|---|---|
| MCC | 25.0 | 0.25 |
| Hydroxypropylmethylcellulose Phthalate (HPMCP) | 10.0 | 0.10 |
| Tartaric Acid | 10.0 | 0.10 |
| Sodium Monoglycerate | 7.5 | 0.075 |
| DSS | 0.5 | 0.005 |
| Levodopa | 35.8 | 0.358 |
| Carbidopa | 11.2 | 0.112 |
| TOTAL | 100.0% | 1.00 kg |

Coating

|  | Weight Percent | Kilograms |
|---|---|---|
| Cellulose Acetate Phthalate (CAP) | 60.0 | 0.60 |
| Ethylcellulose | 25.0 | 0.25 |
| PEG-400 | 15.0 | 0.15 |
| TOTAL | 100.0% | 1.00kg |

The pellets are assayed for levodopa and carbidopa content. It is determined that approximately 223 mg of the pellets contain 80 mg levodopa and 25 mg carbidopa. Dissolution greater than 90% in 30 minutes is also confirmed.

A total of 669 grams of the pellets are blended with 510 grams of the amantadine pellets from Example 2 in a V-blender for 30 minutes at 30 rpm. Gelatin capsules are filled with 393 mg of the mixture and the assays for content are repeated verifying a composition of 100 mg amantadine, 80 mg levodopa, and 25 mg carbidopa.

Example 4

Predicted Dissolution and Plasma Profiles of Amantadine Controlled Release

Using the formulations described above, the dissolution profiles for amantadine were simulated and used to calculate plasma profiles resulting from single or multiple administrations using the pharmacokinetic software, GastroPlus v.4.0.2, from Simulations Plus (see FIG. 2). The initial slope of the dissolution for the sustained release formulation is less than the slope determined for the immediate release formulation (see FIG. 1) and the corresponding serum profile also shows a slower dC/dT (see FIG. 4).

Example 5

Release Profile of Amantadine and L-DOPA (Levodopa/Carbidopa)

Release proportions are shown in the tables below for a combination of amantadine and levodopa/carbidopa. The cumulative fraction is the amount of drug substance released from the formulation matrix to the serum or gut environment (e.g., U.S. Pat. Nos. 4,839,177 or 5,326,570) or as measured with a USP II Paddle system using 0.1N HCl as the dissolution medium.

| Time | AMANTADINE $T\frac{1}{2}$ = 15 hrs cum. fraction A | LEVODOPA/CARBIDOPA $T\frac{1}{2}$ = 1.5 hrs Cum. fraction B |
|---|---|---|
| 0 | 0.00 | 0.00 |
| 0.5 | 0.10 | 0.40 |
| 1.0 | 0.20 | 0.95 |
| 2.0 | 0.35 | 1.00 |
| 4.0 | 0.60 | 1.00 |
| 8.0 | 0.90 | 1.00 |
| 12.0 | 0.98 | 1.00 |

Example 6

Treating Dyskinesia in Patients with Parkinson's Disease

A Parkinson's patient experiencing dyskinesia is administered the composition of Example 3 three times each day to receive 300 mg amantadine, 240 mg levodopa, and 75 mg carbidopa daily. The Parkinsonism is reduced as measured by the UPDRS (Goetz et al., Mov. Disord. 19:1020-8, 2004, incorporated by reference) as is the dyskinesia (Vitale et al., Neurol. Sci. 22:105-6, 2001, incorporated by reference)

Example 7

Animal Models Showing Reduced Dyskinesia, Reduced Levodopa Potential

Figure 8:
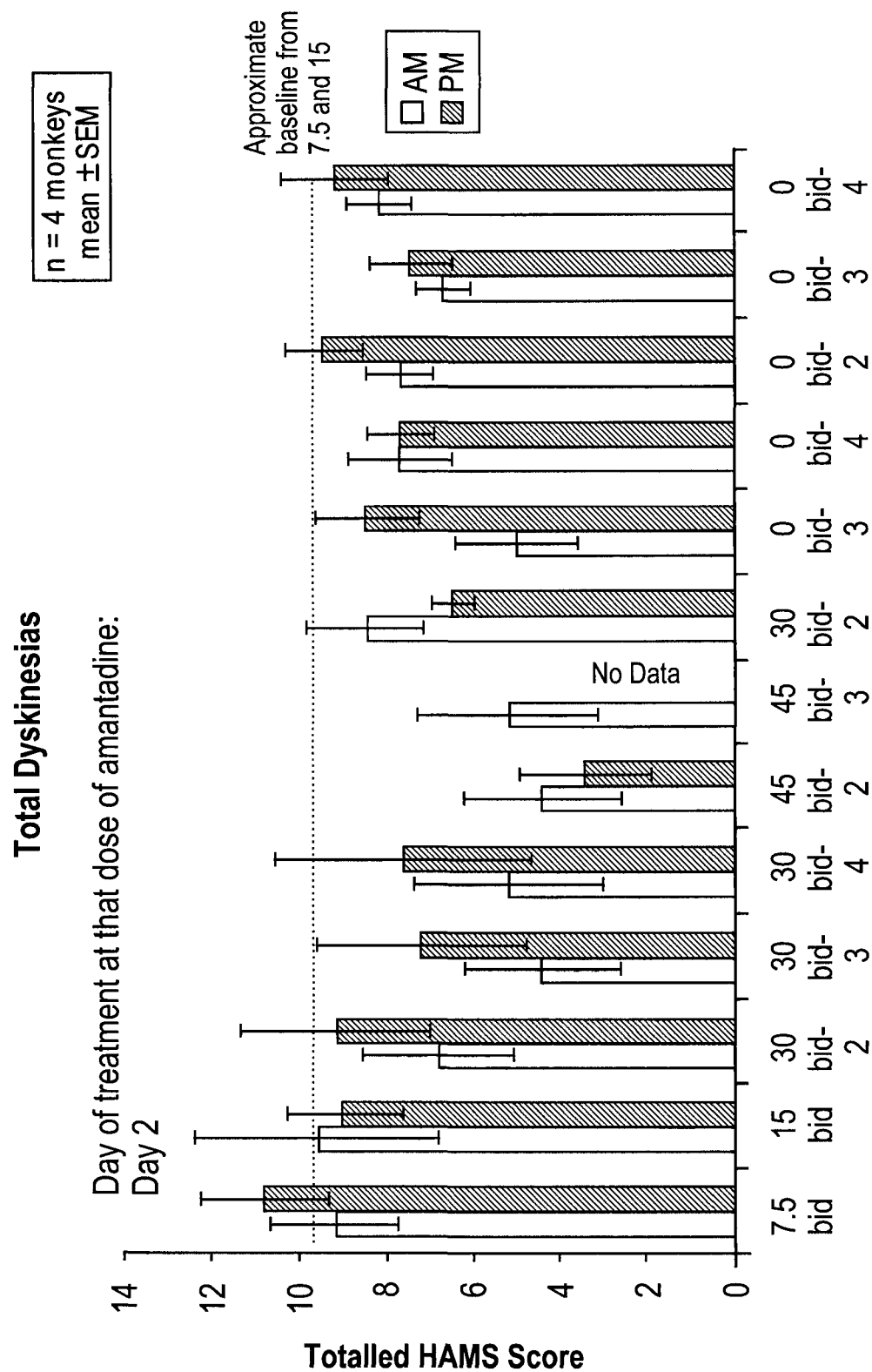
FIG. 8 is a bar graph showing the effects on a primate (squirrel monkey) treated with a combination of levodopa/carbidopa and amantadine.

The following protocol was employed to demonstrate the beneficial effects of the compositions of this invention. Briefly, squirrel monkeys (N=4) were lesioned with MPTP according to the protocol of Di Monte et al. (Mov. Disord. 15: 459-66 (2000)). After 3 months, the monkeys showed full symptoms of Parkinson's disease as measured by a modified UPDRS (Goetz et al., Mov. Disord. 19:1020-8, 2004). Levodopa treatment at approximately 15 mg/kg (with 1.5 mg/kg carbidopa) mg/kg b.i.d. commenced a baseline UPDRS and dyskinesia measurement was established. Amantadine was added to the regimen simultaneously with the levodopa, and the amount raised from 1 mg/kg to 45 mg/kg for four of the squirrel monkeys, corresponding to an estimated 3 μm concentration. As shown in FIG. 8, the combination led to a 60% reduction in dyskinesia. We hypothesize that this translates into a potential 40% reduction in levodopa required to maintain UPDRS.

Example 8

Levodopa Sparing Therapy

The following protocol is employed to determine the optimal reduction of levodopa achieved with the addition of Amantadine to a fixed dose combination product.

Parkinson's DISEASE PROTOCOL SUMMARY NPI MEMANTINE CR MONOTHERAPY
Protocol Number: NPI-Amantadine CR
Study Phase: ⅔
Name of Drug: NPI-Amantadine/C/L
Dosage: 25/100/100 c/l/a given t.i.d. 25/80/100 c/l/a given t.i.d. 25/60/100 c/l/a given t.i.d.
Concurrent Control: 25/100 c/l given t.i.d.
Route: Oral
Subject Population: Male and female patients diagnosed with Parkinson's Disease Hoehn and Yahr score of 2-4
Structure: Parallel-group, three-arm study
Study Term Two weeks
Study Sites: Multi-center 10 centers
Blinding: Double blind
Method of Subject Randomized to one of three treatment groups (3:1)
Assignment:
Total Sample Size: 320 subjects (160 men, 160 women)
Primary Efficacy UPDRS
Endpoints: Abnormal involuntary movement scale (AIMS) 0-4
Secondary Endpoints: Modified Obeso dyskinesia rating scale 0-4 Mini-mental state examination (MMSE); Neuropsychiatric Inventory Score (NPI)
Adverse Events: Monitored and elicited by clinic personnel throughout the study, volunteered by patients Example 9

Pharmaceutical Composition Including Memantine, Levodopa, and Carbidopa

A co-formulation of memantine, levodopa and carbidopa is prepared. This co-formulation matches the absorption properties of levodopa and carbidopa more closely than those of Memantine, thereby extending the effectiveness per dose of levodopa and carbidopa. The co-formulation provides Tmax values to about 4 hours and allows b.i.d. dosing of the combination.

FIG. 6 provides the current single oral dose pharmacokinetic (PK) profiles for levodopa, carbidopa and memantine. FIG. 7 provides idealized pharmacokinetic profiles for the target co-formulation, in which the Tmax values for levodopa and carbidopa more closely match that of Memantine.
Dosage Form: Tablet
Formulation Content: Levodopa 150 mg Carbidopa 37.5 mg Memantine 10 mg
  Excipients: FDA approved excipients and drug release modifiers. Additional embodiments are within the claims.

Example 10

Pharmaceutical Composition Including Extended Release Formulations of Memantine and Levodopa A pulsatile release dosage form for administration of memantine and levodopa may be prepared as three individual compartments. Three individual tablets are compressed, each having a different release profile, followed by encapsulation into a gelatin capsule, which are then closed and sealed. The components of the three tablets are as follows.

| Component | Function | Amount per tablet |
|---|---|---|
| TABLET 1 (IMMEDIATE RELEASE): | | |
| Memantine | Active agent | 8 mg |
| Levodopa | Active agent | 70 mg |
| Dicalcium phosphate dihydrate | Diluent | 26.6 mg |
| Microcrystalline cellulose | Diluent | 26.6 mg |
| Sodium starch glycolate | Disintegrant | 1.2 mg |
| Magnesium Stearate | Lubricant | 0.6 mg |
| TABLET 2 (RELEASE DELAYED 3-5 HOURS FOLLOWING ADMINISTRATION): | | |
| Memantine | Active agent | 8 mg |
| Levodopa | Active agent | 70 mg |
| Dicalcium phosphate dihydrate | Diluent | 26.6 mg |
| Microcrystalline cellulose | Diluent | 26.6 mg |
| Sodium starch glycolate | Disintegrant | 1.2 mg |
| Magnesium Stearate | Lubricant | 0.6 mg |
| Eudragit RS3OD | Delayed release coating material | 4.76 mg |
| Talc | Coating component | 3.3 mg |
| Triethyl citrate | Coating component | 0.95 mg |
| TABLET 3 (RELEASE DELAYED 7-9 HOURS FOLLOWING ADMINISTRATION): | | |
| Memantine | Active agent | 2.5 mg |
| Levodopa | Active agent | 70 mg |
| Dicalcium phosphate dihydrate | Diluent | 26.6 mg |
| Microcrystalline cellulose | Diluent | 26.6 mg |
| Sodium starch glycolate | Disintegrant | 1.2 mg |
| Magnesium Stearate | Lubricant | 0.6 mg |
| Eudragit RS3OD | Delayed release coating material | 6.34 mg |
| Talc | Coating component | 4.4 mg |
| Triethyl citrate | Coating component | 1.27 mg |

The tablets are prepared by wet granulation of the individual drug particles and other core components as may be done using a fluid-bed granulator, or are prepared by direct compression of the admixture of components. Tablet 1 is an immediate release dosage form, releasing the active agents within 1-2 hours following administration. Tablets 2 and 3 are coated with the delayed release coating material as may be carried out using conventional coating techniques such as spray-coating or the like. As will be appreciated by those skilled in the art, the specific components listed in the above tables may be replaced with other functionally equivalent components, e.g., diluents, binders, lubricants, fillers, coatings, and the like.

Oral administration of the capsule to a patient will result in a release profile having three pulses, with initial release of the memantine and levodopa from the first tablet being substantially immediate, release of the memantine and levodopa from the second tablet occurring 3-5 hours following administration, and release of the memantine and levodopa from the third tablet occurring 7-9 hours following administration.

Example 11

Pharmaceutical Composition Including Extended Release Formulations of Memantine, Levodopa, and Carbidopa The method of Example 9 is repeated, except that drug-containing beads are used in place of tablets. Carbidopa is also added in each of the fractions at 25% of the mass of the levodopa. A first fraction of beads is prepared by coating an inert support material such as lactose with the drug which provides the first (immediate release) pulse. A second fraction of beads is prepared by coating immediate release beads with an amount of enteric coating material sufficient to provide a drug release-free period of 3-5 hours. A third fraction of beads is prepared by coating immediate release beads having half the methylphenidate dose of the first fraction of beads with a greater amount of enteric coating material, sufficient to provide a drug release-free period of 7-19 hours. The three groups of beads may be encapsulated or compressed, in the presence of a cushioning agent, into a single pulsatile release tablet.

Alternatively, three groups of drug particles may be provided and coated as above, in lieu of the drug-coated lactose beads.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An osmotic device comprising a core surrounded by a semipermeable membrane having an exit means there through wherein:
   a) the core comprises a mixture of (i) a drug selected from the group consisting of amantadine and pharmaceutically acceptable salts thereof, (ii) an osmotically active component and (iii) at least one other excipient,
   b) the osmotic device further comprises an immediate release overcoat layer comprising the drug,
   c) the osmotic device comprises a total of 50 mg to 500 mg of the drug, and at least 50% of the total drug is provided in the core, and
   d) the osmotic device provides a mean change in amantadine plasma concentration as a function of time (dC/dT) that is less than 40% of the dC/dT provided by the same quantity of an immediate release form of the drug, wherein the dC/dT values are measured in a single dose human pharmacokinetic study over the time period between 0 and 4 hours after administration.

2. An osmotic device comprising a core surrounded by a semipermeable membrane having an exit means there through wherein:
   a) the core comprises a mixture of (i) a drug selected from the group consisting of amantadine and pharmaceutically acceptable salts thereof, (ii) an osmotically active component and (iii) at least one other excipient,
   b) the osmotic device further comprises an immediate release overcoat layer comprising the drug,
   c) the osmotic device comprises a total of 50 mg to 500 mg of the drug, and at least 50% of the total drug is provided in the core, and
   d) the osmotic device provides a mean change in amantadine plasma concentration as a function of time (dC/dT) that is less than 40% of the dC/dT provided by the same quantity of an immediate release form of the drug, wherein the dC/dT values are measured in a single dose human pharmacokinetic study over the time period between administration and Tmax of the immediate release form.

3. An osmotic device comprising a core surrounded by a semipermeable membrane having an exit means there through wherein:
   a) the core comprises a mixture of (i) a drug selected from the group consisting of amantadine and pharmaceutically acceptable salts thereof, (ii) an osmotically active component and (iii) at least one other excipient,
   b) the osmotic device further comprises an immediate release overcoat layer comprising the drug,
   c) the osmotic device comprises a total of 50 mg to 500 mg of the drug, and at least 50% of the total drug is provided in the core, and
   d) the osmotic device provides a mean change in amantadine plasma concentration as a function of time (dC/dT) that is less than 40% of the dC/dT provided by the same quantity of an immediate release form of the drug, wherein the dC/dT of the osmotic device is measured in a single dose human pharmacokinetic study over the time period between 2 hours and 4 hours after administration and the dC/dT provided by the same quantity of the drug in an immediate release form is measured in a single dose human pharmacokinetic study over the time period between administration and Tmax of the immediate release form.

4. The osmotic device of any of claims 1 to 3, wherein the osmotic device comprises a total of 100 mg to 500 mg of the drug.

5. The osmotic device of any of claims 1 to 3, wherein the osmotic device comprises a total of 200 mg to 500 mg of the drug.

6. The osmotic device of any of claims 1 to 3, wherein at least 75% of the drug is provided in the core.

7. The osmotic device of any of claims 1 to 3, wherein at least 90% of the drug is provided in the core.

8. The osmotic device of any of claims 1 to 3, wherein the osmotic device provides a dC/dT that is less than 50% of the dC/dT provided by the same quantity of the drug in an immediate release form.

9. The osmotic device of any of claims 1 to 3, wherein the osmotic device provides a dC/dT that is less than 40% of the dC/dT provided by the same quantity of the drug in an immediate release form.

10. The osmotic device of any of claims 1 to 3, wherein the extent of drug bioavailability is maintained.

11. The osmotic device of any of claims 1 to 3, wherein the osmotic device provides a shift in amantadine Tmax of 2 hours to 16 hours relative to an immediate release form of amantadine, wherein the Tmax is measured in a single dose human pharmacokinetic study.

* * * * *